US010034937B2

(12) United States Patent
Lambers et al.

(10) Patent No.: US 10,034,937 B2
(45) Date of Patent: Jul. 31, 2018

(54) SYNERGISTIC NUTRITIONAL COMPOSITIONS AND USES THEREOF

(71) Applicant: Mead Johnson Nutrition Company, Glenview, IL (US)

(72) Inventors: Teartse Tim Lambers, Nijmegen (NL); Eric A. F. van Tol, Arnhem (NL)

(73) Assignee: Mead Johnson Nutrition Company, Chicago, IL (US)

( * ) Notice: Subject to any disclaimer, the term of this patent is extended or adjusted under 35 U.S.C. 154(b) by 0 days.

(21) Appl. No.: 14/959,107

(22) Filed: Dec. 4, 2015

(65) Prior Publication Data
US 2017/0157242 A1    Jun. 8, 2017

(51) Int. Cl.
| | |
|---|---|
| A61K 39/07 | (2006.01) |
| A61K 39/02 | (2006.01) |
| A61K 39/39 | (2006.01) |
| A61K 35/747 | (2015.01) |
| A61K 31/715 | (2006.01) |
| A61K 31/702 | (2006.01) |
| A61K 31/19 | (2006.01) |
| A61K 39/35 | (2006.01) |
| A23L 1/29 | (2006.01) |
| A23L 1/305 | (2006.01) |
| A23L 1/30 | (2006.01) |
| A23L 1/308 | (2006.01) |
| A61K 35/00 | (2006.01) |
| A61K 39/00 | (2006.01) |

(52) U.S. Cl.
CPC .............. *A61K 39/39* (2013.01); *A23L 1/296* (2013.01); *A23L 1/308* (2013.01); *A23L 1/3008* (2013.01); *A23L 1/3014* (2013.01); *A23L 1/3053* (2013.01); *A61K 31/19* (2013.01); *A61K 31/702* (2013.01); *A61K 31/715* (2013.01); *A61K 35/747* (2013.01); *A61K 39/35* (2013.01); *A23V 2002/00* (2013.01); *A23Y 2220/73* (2013.01); *A61K 2035/115* (2013.01); *A61K 2039/542* (2013.01); *A61K 2039/55* (2013.01); *A61K 2039/55511* (2013.01); *A61K 2039/55594* (2013.01); *A61K 2039/577* (2013.01)

(58) Field of Classification Search
USPC ................................................. 426/590, 801
See application file for complete search history.

(56) References Cited

U.S. PATENT DOCUMENTS

| | | |
|---|---|---|
| 4,791,193 A | 12/1988 | Okonogi et al. |
| 5,032,399 A | 7/1991 | Gorbach et al. |
| 5,849,885 A | 12/1998 | Nuyens |
| 5,861,491 A | 1/1999 | Nuijens |
| 5,919,913 A | 7/1999 | Nuyens |
| 6,620,326 B1 | 9/2003 | Lihme |
| 6,977,046 B2 | 12/2005 | Hubbuch |
| 7,368,141 B2 | 5/2008 | Lihme |
| 7,812,138 B2 | 10/2010 | Lihme et al. |
| 7,867,541 B2 | 1/2011 | McMahon |
| 7,951,410 B2 | 5/2011 | McMahon |
| 8,119,155 B2 | 2/2012 | Speelmans et al. |
| 8,452,955 B2 | 4/2013 | Wittke |
| 8,557,320 B2 * | 10/2013 | Petschow ............. A61K 31/721 426/590 |
| 8,771,674 B2 | 7/2014 | Sprenger |
| 9,119,838 B2 | 9/2015 | Knippels et al. |
| 9,255,062 B2 | 2/2016 | Canani et al. |
| 2003/0203004 A1 | 10/2003 | Kelm et al. |
| 2003/0203114 A1 | 10/2003 | Nash et al. |
| 2008/0213341 A1 | 9/2008 | Begli et al. |
| 2009/0029020 A1 | 1/2009 | Strassburger |
| 2009/0136615 A1 | 5/2009 | Speelmans et al. |
| 2011/0098319 A1 | 4/2011 | Canani et al. |
| 2011/0217402 A1 | 9/2011 | van Tol et al. |
| 2011/0313040 A1 | 12/2011 | Kong et al. |
| 2013/0122182 A1 | 5/2013 | Lai et al. |
| 2013/0243797 A1 | 9/2013 | Sprenger |
| 2013/0251829 A1 | 9/2013 | van Tol et al. |
| 2014/0255538 A1 | 9/2014 | Banavara et al. |
| 2014/0271553 A1 | 9/2014 | Hondmann et al. |
| 2014/0271554 A1 | 9/2014 | Hondmann et al. |
| 2015/0119322 A1 | 4/2015 | Chichlowski et al. |
| 2015/0231213 A1 | 8/2015 | Chichlowski et al. |
| 2015/0305384 A1 | 10/2015 | Chichlowski et al. |
| 2016/0305384 A1 | 10/2016 | Avireddi et al. |
| 2017/0007629 A1 | 1/2017 | Kuang et al. |

FOREIGN PATENT DOCUMENTS

| | | |
|---|---|---|
| EP | 1103259 | 5/2001 |
| EP | 2268605 | 1/2011 |
| EP | 2289505 | 3/2011 |

(Continued)

OTHER PUBLICATIONS

Ahanchian, H., et al., "Synbiotics in Children with Cow's Milk Allergy: A Randomized Controlled Trial," Iran J. Pediatr, Feb. 2014; vol. 24 (No. 1), pp: 29-34.
Farid, R., et al., "Effect of a New Synbiotic Mixture on Atopic Dermatitis in Children: a Randomized-Controlled Trial," Iran J. Pediatr, Jun. 2011; vol. 21 (No. 2), pp: 225-230.
Schouten, B., et al., Cow Milk Allergy Symptoms Are Reduced in Mice Fed Dietary Synbiotics during Oral Sensitization with Whey1, J. Nutr. 139: 1398-1403, 2009.
Wu, K., et al., "Lactobacillus salivarius plus fructo-oligosaccharide is superior to fructo-oligosaccharide alone for treating children with moderate to severe atopic dermatitis: a double-blind, randomized, clinical trial of efficacy and safety," British Association of Dermatologists 2012 166, pp. 129-136.

(Continued)

*Primary Examiner* — Rodney P Swartz
(74) *Attorney, Agent, or Firm* — OspreyIP, pllc; James R. Cartiglia

(57) ABSTRACT

Provided are nutritional compositions comprising a combination of a probiotic, dietary butyrate and/or a component for stimulating butyrate production in the human gut. Further disclosed are methods of accelerating tolerance to cow's milk allergy in a pediatric subject by providing said nutritional compositions to a target subject.

7 Claims, No Drawings

(56) References Cited

FOREIGN PATENT DOCUMENTS

| EP | 2716167 | 4/2014 |
|---|---|---|
| RU | 2373769 | 11/2009 |
| WO | 199200799 | 1/1992 |
| WO | 199218237 | 10/1992 |
| WO | 199717132 | 5/1997 |
| WO | 2006115412 | 11/2006 |
| WO | 2009130735 | 10/2009 |
| WO | 2009154463 | 12/2009 |
| WO | 2012131069 | 4/2012 |
| WO | 2013062402 | 5/2013 |
| WO | 2013191533 | 12/2013 |
| WO | 2015078506 | 6/2015 |

OTHER PUBLICATIONS

Yadomae, T., Structure and biological activities of fungal beta-1,3-glucans. Yakugaku Zasshi. 2000;120:413-431.
Zhong, J., et al., "Studies on the effects of polydextrose intake on physiologic functions in Chinese people1-3," Am J. Clin Nurt 2000;72:1503-9.
Burks, W.A., et al., "Functional effects, including effects on gut microbiota, of an amino acid-based formula with synbiotics in cow's milk allergic infants," Allergy, vol. 69, No. Supplment 99, Sep. 2014, p. 574, XP055328769.
Canani, R., et al., "Lactobacillus rhamnosus GG-supplemented formula expands butyrate-producing bacterial strains in food allergic infants," The ISME Journal vol. 10, No. 3, Sep. 22, 2015, pp. 742-750, SP055328755.
Huang, H., et al., "Regulation of TWIK-related potassium channel-1 (Trek 1) restitutes intestinal epithelial barrier function," Cellular & Molecular Immunology, vol. 13, No. 1, Feb. 16, 2015, pp. 110-118, XP055328911.
Huang, H., et al., "Regulation of Twik-related potassium channel-1 (Trek 1) restitutes intestinal epithelial barrier unction," Cellular & Molecular Immunology, vol. 13, No. 1, Feb. 16, 2015, pp. 110-118, XP055328911.
Conley, B., et al., "Phase I Study of the Orally Administered Butyrate Prodrug, Tributyrin, in Patients with Solid Tumors1," Clinical Cancer Research, vol. 4, Mar. 1998, 629-634.
Edelman, M., et al., "Clinical and pharmacologic study of tributyrin: an oral butyrate prodrug," Cancer Chemother Pharmacol (2003) 51: 439-4-44.
Rehni, A., et al., "Modulation of histone deacetylase attenuates naloxone-precipitated opioid withdrawal syndrome," Naunyn-Schmiedeberg's Arch Pharmacol, Feb. 25, 2012, DOI 10.1007/s00210-012-0739-x.
Vijay, N., et al., "Role of Monocarboxylate Transporters in Drug Delivery to the Brain," Curr Pharm Des. 2014 ; 20 (10): 1487-1498.
Furusawa, Y. et al., "Commensal microbe-derived butyrate induces the differentiation of colonic regulatory T cells" Nature, Dec. 19, 2013; 504 (7480): 446-50.
Nylund, L. et al. "Severity of atopic disease inversely correlates with intestinal microbiota diversity and butyrate-producing bacteria," Allergy 70 (2015), 241-244.
Paparo, L. et al. "The Influence of Early Life Nutrition on Epigenetic Regulatory Mechanisms of the Immune System", Nutrients 2014, 6, 4706-4719.
Weise, C. et al. "Dietary polyunsaturated fatty acids and non-digestible oligosaccharides reduce dermatitis in mice" Pediatric Allergy and Immunology 24 (2013) 361-367.
Arnoldussen, I., et al., "Early intake of long-chain polyunsaturated fatty acids preserves brain structure and function in diet-induced obesity," J Nutr Biochem. 2016; 30:177-88.
Canfora, E., et al., "Short-chain fatty acids in control of body weight and insulin sensitivity," Canfora, E. E. et al. Nat Rev. Endocrinol. 11,577-591 (2015); published online Aug. 11, 2015; doi:10.1038/nrendo.2015.128.
Cani, P., et al., "The gut microbiome as therapeutic target," Pharmacology & Therapeutics 130 (2011) 202-212.
Croze, M. et al., "Abnormalities in myo-inositol metabolism associated with type 2 diabetes in mice fed a high-fat diet: benefits of a dietary myo-inositol supplementation," British Journal of Nutrition (2015), 113,1862-1875.
Croze, M. et al., "Potential role and therapeutic interests of myo-inositol in metabolic diseases," Biochimie 95 (2013) 1811e1827.
Gao, Z., et al., "Butyrate Improves Insulin Sensitivity and Increases Energy Expenditure in Mice," Diabetes Jul. 2008; 58(7): 1509-1517.
Jeffrey, A., et al., "Adiponectin in childhood," International Journal of Pediatric Obesity, 2008;3:130-140.
Kato, S., et al., "Effects of Na-butyrate supplementation in milk formula on plasma concentrations of GH and insulin, and on rumen papilla development in calves," Journal of Endocrinology (2011) 211, 241-248.
Li, Y., et al., "Lactoferrin Dampens High-Fructose Corn Syrup-Induced Hepatic Manifestations of the Metabolic Syndrome in a Murine Model," PLoS ONE 9(5): e97341. doi:10.1371/journal.pone.0097341.
Moreno-Naverrete, J., et al., "Lactoferrin gene knockdown leads to similar effects to iron chelation in human adipocytes," J. Cell. Mol. Med. vol. 18, No. 3, 2014 pp. 391-395.
Prentice, et al., "Human milk short chain fatty acid composition is associated with infancy adiposity outcomes," JPGN, vol. 62, Supplement 1, 2016.
Reis, A., et al., "Vitamin D endocrine system and the genetic susceptibility to diabetes, obesity and vascular disease. A review of evidence," Diabetes Metab 2005;31:318-325.
Romacho, T., et al., "Nutritional ingredients modulate adipokine secretion and inflammation in human primary adipocytes," Nutrients. Jan, 26, 2015;7(2):865-86.
Shi, J., et al., "Metabolic effects of lactoferrin during energy restriction and weight regain in diet-induced obese mice," Journal of Functional Foods 4 (2012) 66-78.
Timby, N., et al., "Cardiovascular risk markers until 12 mo of age in infants fed a formula supplemented with bovine milk fat globule membranes," Pediatric Research vol. 76, No. 4, Oct. 2014.
Timby, N., et al., "Neurodevelopment, nutrition, and growth until 12 mo of age in infants fed a low-energy, low-protein formula supplemented with bovine milk fat globule membranes: a randomized controlled trial1-3," Am J Clin Nutr 2014;99:860-8.
Vinolo, M., et al., "Tributyrin attenuates obesity-associated inflammation and insulin resistance in high-fat-fed mice," Am J Physiol Endocrinol Metab 303: E272-E282, 2012.
Wielinga, P., et al. "Arachidonic acid/docosahexaenoic acid-supplemented diet in early life reduces body weight gain, plasma lipids, and adiposity in later life in ApoE*3Leiden mice," Mol Nutr Food Res. Jul. 2012; 56(7):1081-9.
Mansson, HL et al. In "Fatty Acids in Bovine Milk Fat" : Report, Swedish Dairy Association, Lund, Sweden, 2008: Food & Nutrition Research, pp. 1-3, 2008.
Ogasa, The content of free and bound inositol in human and cow's milk, J. Nutr. Science, Vitaminol, 21, 129-135, 1975.
Coppa, "Prebiotics in human milk: a review" Digestive and Liver Disease, 38 Suppl. 2 (2006) S291-S94.
Haug, "Bovine milk in human nutrition: a reivew" Lipids in Health and Diseases, 2007, 6:25.
Hamzelou, "Cow's milk has vital prebiotic for a healthy baby's microbiome" New Scientist, Apr. 15, 2016.
Parodi "Cow's milk fat components as potenital anticarcinogenic agents" J Nutr. 127: 1055-1060, 1997.
Organic Pastures Whole Milk, Jay-Russell, 2011, Food Safety News, Raw Milk Myths—Busted.
Tiffany, "Transforming ordinary yogurt into homemade Greek yogurt and whey" website—Don't Waste the Crumbs http://dontwastethecrumbs.com/2013/10/transforming-oridinary-yogurt-into-homemade-greek-yogurt-and-whey/.
Jauy, Term infant studies of DHA and ARA supplementation on neurodevelopment: Results of controlled trials, J. Pediatr 2003: 143:S17-S25.
El-Khoury, Beta Glucan: Health Benefits in Obesity and Metabolic Syndrome, J Nutr. Metab. 2012; 2012.

\* cited by examiner

SEQUENCE LISTING

<160> NUMBER OF SEQ ID NOS: 64

<210> SEQ ID NO 1
<211> LENGTH: 8
<212> TYPE: PRT
<213> ORGANISM: Bos taurus

<400> SEQUENCE: 1

Ala Ile Asn Pro Ser Lys Glu Asn
1               5

<210> SEQ ID NO 2
<211> LENGTH: 5
<212> TYPE: PRT
<213> ORGANISM: Bos taurus

<400> SEQUENCE: 2

Ala Pro Phe Pro Glu
1               5

<210> SEQ ID NO 3
<211> LENGTH: 6
<212> TYPE: PRT
<213> ORGANISM: Bos taurus

<400> SEQUENCE: 3

Asp Ile Gly Ser Glu Ser
1               5

<210> SEQ ID NO 4
<211> LENGTH: 7
<212> TYPE: PRT
<213> ORGANISM: Bos taurus

<400> SEQUENCE: 4

Asp Lys Thr Glu Ile Pro Thr
1               5

<210> SEQ ID NO 5
<211> LENGTH: 5
<212> TYPE: PRT
<213> ORGANISM: Bos taurus

<400> SEQUENCE: 5

Asp Met Glu Ser Thr
1               5

<210> SEQ ID NO 6
<211> LENGTH: 4
<212> TYPE: PRT
<213> ORGANISM: Bos taurus

<400> SEQUENCE: 6

Asp Met Pro Ile
1

<210> SEQ ID NO 7
<211> LENGTH: 4
<212> TYPE: PRT
<213> ORGANISM: Bos taurus

<400> SEQUENCE: 7

Asp Val Pro Ser
1

```
<210> SEQ ID NO 8
<211> LENGTH: 7
<212> TYPE: PRT
<213> ORGANISM: Bos taurus

<400> SEQUENCE: 8

Glu Thr Ala Pro Val Pro Leu
1               5

<210> SEQ ID NO 9
<211> LENGTH: 6
<212> TYPE: PRT
<213> ORGANISM: Bos taurus

<400> SEQUENCE: 9

Phe Pro Gly Pro Ile Pro
1               5

<210> SEQ ID NO 10
<211> LENGTH: 7
<212> TYPE: PRT
<213> ORGANISM: Bos taurus

<400> SEQUENCE: 10

Phe Pro Gly Pro Ile Pro Asn
1               5

<210> SEQ ID NO 11
<211> LENGTH: 4
<212> TYPE: PRT
<213> ORGANISM: Bos taurus

<400> SEQUENCE: 11

Gly Pro Phe Pro
1

<210> SEQ ID NO 12
<211> LENGTH: 4
<212> TYPE: PRT
<213> ORGANISM: Bos taurus

<400> SEQUENCE: 12

Gly Pro Ile Val
1

<210> SEQ ID NO 13
<211> LENGTH: 9
<212> TYPE: PRT
<213> ORGANISM: Bos taurus

<400> SEQUENCE: 13

Ile Gly Ser Glu Ser Thr Glu Asp Gln
1               5

<210> SEQ ID NO 14
<211> LENGTH: 8
<212> TYPE: PRT
<213> ORGANISM: Bos taurus

<400> SEQUENCE: 14

Ile Gly Ser Ser Ser Glu Glu Ser
1               5

<210> SEQ ID NO 15
```

```
<211> LENGTH: 9
<212> TYPE: PRT
<213> ORGANISM: Bos taurus

<400> SEQUENCE: 15

Ile Gly Ser Ser Ser Glu Glu Ser Ala
1               5

<210> SEQ ID NO 16
<211> LENGTH: 6
<212> TYPE: PRT
<213> ORGANISM: Bos taurus

<400> SEQUENCE: 16

Ile Asn Pro Ser Lys Glu
1               5

<210> SEQ ID NO 17
<211> LENGTH: 5
<212> TYPE: PRT
<213> ORGANISM: Bos taurus

<400> SEQUENCE: 17

Ile Pro Asn Pro Ile
1               5

<210> SEQ ID NO 18
<211> LENGTH: 6
<212> TYPE: PRT
<213> ORGANISM: Bos taurus

<400> SEQUENCE: 18

Ile Pro Asn Pro Ile Gly
1               5

<210> SEQ ID NO 19
<211> LENGTH: 9
<212> TYPE: PRT
<213> ORGANISM: Bos taurus

<400> SEQUENCE: 19

Ile Pro Pro Leu Thr Gln Thr Pro Val
1               5

<210> SEQ ID NO 20
<211> LENGTH: 4
<212> TYPE: PRT
<213> ORGANISM: Bos taurus

<400> SEQUENCE: 20

Ile Thr Ala Pro
1

<210> SEQ ID NO 21
<211> LENGTH: 4
<212> TYPE: PRT
<213> ORGANISM: Bos taurus

<400> SEQUENCE: 21

Ile Val Pro Asn
1

<210> SEQ ID NO 22
<211> LENGTH: 7
<212> TYPE: PRT
```

<213> ORGANISM: Bos taurus

<400> SEQUENCE: 22

Lys His Gln Gly Leu Pro Gln
1               5

<210> SEQ ID NO 23
<211> LENGTH: 5
<212> TYPE: PRT
<213> ORGANISM: Bos taurus

<400> SEQUENCE: 23

Leu Asp Val Thr Pro
1               5

<210> SEQ ID NO 24
<211> LENGTH: 6
<212> TYPE: PRT
<213> ORGANISM: Bos taurus

<400> SEQUENCE: 24

Leu Glu Asp Ser Pro Glu
1               5

<210> SEQ ID NO 25
<211> LENGTH: 5
<212> TYPE: PRT
<213> ORGANISM: Bos taurus

<400> SEQUENCE: 25

Leu Pro Leu Pro Leu
1               5

<210> SEQ ID NO 26
<211> LENGTH: 6
<212> TYPE: PRT
<213> ORGANISM: Bos taurus

<400> SEQUENCE: 26

Met Glu Ser Thr Glu Val
1               5

<210> SEQ ID NO 27
<211> LENGTH: 11
<212> TYPE: PRT
<213> ORGANISM: Bos taurus

<400> SEQUENCE: 27

Met His Gln Pro His Gln Pro Leu Pro Pro Thr
1               5                   10

<210> SEQ ID NO 28
<211> LENGTH: 5
<212> TYPE: PRT
<213> ORGANISM: Bos taurus

<400> SEQUENCE: 28

Asn Ala Val Pro Ile
1               5

<210> SEQ ID NO 29
<211> LENGTH: 5
<212> TYPE: PRT
<213> ORGANISM: Bos taurus

<400> SEQUENCE: 29

Asn Glu Val Glu Ala
1               5

<210> SEQ ID NO 30
<211> LENGTH: 6
<212> TYPE: PRT
<213> ORGANISM: Bos taurus

<400> SEQUENCE: 30

Asn Gln Glu Gln Pro Ile
1               5

<210> SEQ ID NO 31
<211> LENGTH: 5
<212> TYPE: PRT
<213> ORGANISM: Bos taurus

<400> SEQUENCE: 31

Asn Val Pro Gly Glu
1               5

<210> SEQ ID NO 32
<211> LENGTH: 6
<212> TYPE: PRT
<213> ORGANISM: Bos taurus

<400> SEQUENCE: 32

Pro Phe Pro Gly Pro Ile
1               5

<210> SEQ ID NO 33
<211> LENGTH: 6
<212> TYPE: PRT
<213> ORGANISM: Bos taurus

<400> SEQUENCE: 33

Pro Gly Pro Ile Pro Asn
1               5

<210> SEQ ID NO 34
<211> LENGTH: 8
<212> TYPE: PRT
<213> ORGANISM: Bos taurus

<400> SEQUENCE: 34

Pro His Gln Pro Leu Pro Pro Thr
1               5

<210> SEQ ID NO 35
<211> LENGTH: 5
<212> TYPE: PRT
<213> ORGANISM: Bos taurus

<400> SEQUENCE: 35

Pro Ile Thr Pro Thr
1               5

<210> SEQ ID NO 36
<211> LENGTH: 4
<212> TYPE: PRT
<213> ORGANISM: Bos taurus

<400> SEQUENCE: 36

Pro Asn Pro Ile
1

<210> SEQ ID NO 37
<211> LENGTH: 6
<212> TYPE: PRT
<213> ORGANISM: Bos taurus

<400> SEQUENCE: 37

Pro Asn Ser Leu Pro Gln
1               5

<210> SEQ ID NO 38
<211> LENGTH: 8
<212> TYPE: PRT
<213> ORGANISM: Bos taurus

<400> SEQUENCE: 38

Pro Gln Leu Glu Ile Val Pro Asn
1               5

<210> SEQ ID NO 39
<211> LENGTH: 7
<212> TYPE: PRT
<213> ORGANISM: Bos taurus

<400> SEQUENCE: 39

Pro Gln Asn Ile Pro Pro Leu
1               5

<210> SEQ ID NO 40
<211> LENGTH: 6
<212> TYPE: PRT
<213> ORGANISM: Bos taurus

<400> SEQUENCE: 40

Pro Val Leu Gly Pro Val
1               5

<210> SEQ ID NO 41
<211> LENGTH: 4
<212> TYPE: PRT
<213> ORGANISM: Bos taurus

<400> SEQUENCE: 41

Pro Val Pro Gln
1

<210> SEQ ID NO 42
<211> LENGTH: 5
<212> TYPE: PRT
<213> ORGANISM: Bos taurus

<400> SEQUENCE: 42

Pro Val Val Val Pro
1               5

<210> SEQ ID NO 43
<211> LENGTH: 6
<212> TYPE: PRT
<213> ORGANISM: Bos taurus

<400> SEQUENCE: 43

Pro Val Val Val Pro Pro
1               5

```
<210> SEQ ID NO 44
<211> LENGTH: 11
<212> TYPE: PRT
<213> ORGANISM: Bos taurus

<400> SEQUENCE: 44

Ser Ile Gly Ser Ser Glu Glu Ser Ala Glu
1               5                   10

<210> SEQ ID NO 45
<211> LENGTH: 7
<212> TYPE: PRT
<213> ORGANISM: Bos taurus

<400> SEQUENCE: 45

Ser Ile Ser Ser Ser Glu Glu
1               5

<210> SEQ ID NO 46
<211> LENGTH: 11
<212> TYPE: PRT
<213> ORGANISM: Bos taurus

<400> SEQUENCE: 46

Ser Ile Ser Ser Ser Glu Glu Ile Val Pro Asn
1               5                   10

<210> SEQ ID NO 47
<211> LENGTH: 7
<212> TYPE: PRT
<213> ORGANISM: Bos taurus

<400> SEQUENCE: 47

Ser Lys Asp Ile Gly Ser Glu
1               5

<210> SEQ ID NO 48
<211> LENGTH: 6
<212> TYPE: PRT
<213> ORGANISM: Bos taurus

<400> SEQUENCE: 48

Ser Pro Pro Glu Ile Asn
1               5

<210> SEQ ID NO 49
<211> LENGTH: 7
<212> TYPE: PRT
<213> ORGANISM: Bos taurus

<400> SEQUENCE: 49

Ser Pro Pro Glu Ile Asn Thr
1               5

<210> SEQ ID NO 50
<211> LENGTH: 7
<212> TYPE: PRT
<213> ORGANISM: Bos taurus

<400> SEQUENCE: 50

Thr Asp Ala Pro Ser Phe Ser
1               5
```

<210> SEQ ID NO 51
<211> LENGTH: 5
<212> TYPE: PRT
<213> ORGANISM: Bos taurus

<400> SEQUENCE: 51

Thr Glu Asp Glu Leu
1               5

<210> SEQ ID NO 52
<211> LENGTH: 6
<212> TYPE: PRT
<213> ORGANISM: Bos taurus

<400> SEQUENCE: 52

Val Ala Thr Glu Glu Val
1               5

<210> SEQ ID NO 53
<211> LENGTH: 5
<212> TYPE: PRT
<213> ORGANISM: Bos taurus

<400> SEQUENCE: 53

Val Leu Pro Val Pro
1               5

<210> SEQ ID NO 54
<211> LENGTH: 4
<212> TYPE: PRT
<213> ORGANISM: Bos taurus

<400> SEQUENCE: 54

Val Pro Gly Glu
1

<210> SEQ ID NO 55
<211> LENGTH: 6
<212> TYPE: PRT
<213> ORGANISM: Bos taurus

<400> SEQUENCE: 55

Val Pro Gly Glu Ile Val
1               5

<210> SEQ ID NO 56
<211> LENGTH: 6
<212> TYPE: PRT
<213> ORGANISM: Bos taurus

<400> SEQUENCE: 56

Val Pro Ile Thr Pro Thr
1               5

<210> SEQ ID NO 57
<211> LENGTH: 4
<212> TYPE: PRT
<213> ORGANISM: Bos taurus

<400> SEQUENCE: 57

Val Pro Ser Glu
1

<210> SEQ ID NO 58
<211> LENGTH: 9

<212> TYPE: PRT
<213> ORGANISM: Bos taurus

<400> SEQUENCE: 58

Val Val Pro Pro Phe Leu Gln Pro Glu
1               5

<210> SEQ ID NO 59
<211> LENGTH: 5
<212> TYPE: PRT
<213> ORGANISM: Bos taurus

<400> SEQUENCE: 59

Val Val Val Pro Pro
1               5

<210> SEQ ID NO 60
<211> LENGTH: 6
<212> TYPE: PRT
<213> ORGANISM: Bos taurus

<400> SEQUENCE: 60

Tyr Pro Phe Pro Gly Pro
1               5

<210> SEQ ID NO 61
<211> LENGTH: 8
<212> TYPE: PRT
<213> ORGANISM: Bos taurus

<400> SEQUENCE: 61

Tyr Pro Phe Pro Gly Pro Ile Pro
1               5

<210> SEQ ID NO 62
<211> LENGTH: 9
<212> TYPE: PRT
<213> ORGANISM: Bos taurus

<400> SEQUENCE: 62

Tyr Pro Phe Pro Gly Pro Ile Pro Asn
1               5

<210> SEQ ID NO 63
<211> LENGTH: 5
<212> TYPE: PRT
<213> ORGANISM: Bos taurus

<400> SEQUENCE: 63

Tyr Pro Ser Gly Ala
1               5

<210> SEQ ID NO 64
<211> LENGTH: 5
<212> TYPE: PRT
<213> ORGANISM: Bos taurus

<400> SEQUENCE: 64

Tyr Pro Val Glu Pro
1               5

SYNERGISTIC NUTRITIONAL COMPOSITIONS AND USES THEREOF

TECHNICAL FIELD

The present disclosure relates generally to nutritional compositions comprising a combination of polydextrose ("PDX"), galacto-oligosaccharides ("GOS"), and *Lactobacillus rhamnosus* GG ("LGG") or compositions comprising LGG and phenylalanine-butyramide ("FBA"). The nutritional compositions are suitable for administration to pediatric subjects. Further, disclosed are methods for reducing risk for allergic sensitization/prevention of allergic diseases, accelerating tolerance to cow's milk allergy and the dietary management of food allergy via administering the compositions disclosed herein. The disclosed nutritional compositions may provide additive and or/synergistic beneficial health effects.

BACKGROUND ART

Food allergies, such as allergy to cow's milk protein, soy protein, rice protein and peanuts, are being recognized as an increasing problem. Cow's milk protein allergy ("CMA") is the most common food allergy in early childhood and affects 2-3% of young children with a range of immunoglobulin (Ig-E) and non Ig-E mediated syndromes. Food allergies continue to be a growing health concern with an increasing prevalence and severity, potential increase of atopic disease in later life, risk of persistence, and functional gastrointestinal disorders. Thus, there is a strong need to develop effective methods for supporting resistance to such allergies.

Typically, the first step of treatment of CMA is the rapid resolution of symptoms, with elimination of cow's milk protein from the diet being the only proven treatment. While certain hydrolyzed protein formulas have been used to avoid CMA, there is a need for nutritional compositions, especially for infants, including components that are capable of further accelerating tolerance acquisition to cow's milk.

Accordingly, provided herein are nutritional compositions that accelerate tolerance to cow's milk allergy. Further provided are compositions for the dietary management of food allergies.

BRIEF SUMMARY

Briefly, the present disclosure is directed, in an embodiment, to a nutritional composition that includes a synbiotic combination of a prebiotic composition comprising PDX and GOS in combination with LGG. Additionally, the disclosure provides, in an embodiment, a nutritional composition comprising dietary butyrate and LGG. In some embodiments, the nutritional compositions include a component which can stimulate the production of endogenous short chain fatty acid ("SCFA") including butyrate in the human gut. In some embodiments, the dietary butyrate may be provided directly by nutrition in the form of encapsulated butyrate, phenylalanine-butyramide ("FBA") or enriched lipid fractions from milk.

The present disclosure further provides methods for accelerating tolerance to cow's milk allergy in a target subject via administering the nutritional compositions disclosed herein to the target subject. Further provided are methods for the dietary management of allergy, such as cow's milk allergy, via administering the nutritional composition disclosed herein to the target subject.

It is to be understood that both the foregoing general description and the following detailed description present embodiments of the disclosure and are intended to provide an overview or framework for understanding the nature and character of the disclosure as it is claimed. The description serves to explain the principles and operations of the claimed subject matter. Other and further features and advantages of the present disclosure will be readily apparent to those skilled in the art upon a reading of the following disclosure.

DETAILED DESCRIPTION

Reference now will be made in detail to the embodiments of the present disclosure, one or more examples of which are set forth herein below. Each example is provided by way of explanation of the nutritional composition of the present disclosure and is not a limitation. In fact, it will be apparent to those skilled in the art that various modifications and variations can be made to the teachings of the present disclosure without departing from the scope of the disclosure. For instance, features illustrated or described as part of one embodiment, can be used with another embodiment to yield a still further embodiment.

Thus, it is intended that the present disclosure covers such modifications and variations as come within the scope of the appended claims and their equivalents. Other objects, features and aspects of the present disclosure are disclosed in or are apparent from the following detailed description. It is to be understood by one of ordinary skill in the art that the present discussion is a description of exemplary embodiments only and is not intended as limiting the broader aspects of the present disclosure.

The present disclosure relates generally to nutritional compositions comprising dietary butyrate and a probiotic comprising LGG. In some embodiments, provided are nutritional compositions comprising a prebiotic comprising PDX and GOS and LGG. Additionally, the disclosure relates to methods for accelerating tolerance to cow's milk allergy or methods for the dietary management of allergy in target subjects.

"Allergy" as used herein is defined as an "abnormal hypersensitivity to a substance which is normally tolerated and generally considered harmless." There are two basic phases involved with the allergic response. The first stage involves the development of the early phase of an immediate-type hypersensitivity response to allergens. The first time an allergen meets the immune system, no allergic reaction occurs. Instead, the immune system prepares itself for future encounters with the allergen. Macrophages, which are scavenger cells, surround and break up the invading allergen. The macrophages then display the allergen fragments on their cell walls to T lymphocytes, which are the main orchestrators of the body's immune reaction. This cognitive signal plus several non-cognitive signals (e.g. cytokines) activate the naïve T-cells and instruct the T-cell differentiation into T-cell effector subpopulations. The key players in the allergic cascade are T-cells of the Th-2 phenotype (TH-2). TH-2 type T-cells are characterized by the secretion of several cytokines including interleukin-4 (IL-4), IL-5 and IL-13. The cytokines IL-4 and IL-13 then activate B lymphocytes which produce antibodies of the subclass E (IgE). IgE antibodies are directed against the particular allergen. The interaction of specific IgE antibodies on the surface of effector cells (mast cells and basophils) with an allergen triggers the early phase of immediate type hypersensitivity responses.

This mast cell activation usually occurs within minutes after the second exposure to an allergen. IgE antibodies on mast cells, constructed during the sensitization phase, recognize the allergen and bind to the invader. Once the allergen is bound to the receptor, granules in the mast cells release their contents. These contents, or mediators, are proinflammatory substances such as histamine, platelet-activating factor, prostaglandins, cytokines and leukotrienes. These mediators actually trigger the allergy attack. Histamine stimulates mucus production and causes redness, swelling, and inflammation. Prostaglandins constrict airways and enlarge blood vessels.

The second phase of the allergic immune response is characterized by infiltration of inflammatory cells, such as eosinophils, into the airways after an allergen exposure. An important linkage between sensitization and inflammation is represented by T-cells that secrete mediators not only involved in IgE synthesis, but also responsible for eosinophil recruitment, activation and survival. The tissue mast cells and neighboring cells produce chemical messengers that signal circulating basophils, eosinophils, and other cells to migrate into that tissue and help fight the foreign material. Eosinophils secrete chemicals of their own that sustain inflammation, cause tissue damage, and recruit yet more immune cells. This phase can occur anywhere between several hours and several days after the allergen exposure and can last for hours and even days.

"Nutritional composition" means a substance or formulation that satisfies at least a portion of a subject's nutrient requirements. The terms "nutritional(s)", "nutritional formula(s)", "enteral nutritional(s)", and "nutritional supplement(s)" are used as non-limiting examples of nutritional composition(s) throughout the present disclosure. Moreover, "nutritional composition(s)" may refer to liquids, powders, gels, pastes, solids, concentrates, suspensions, or ready-to-use forms of enteral formulas, oral formulas, formulas for infants, formulas for pediatric subjects, formulas for children, growing-up milks and/or formulas for adults.

"Pediatric subject" means a human less than 13 years of age. In some embodiments, a pediatric subject refers to a human subject that is between birth and 8 years old. In other embodiments, a pediatric subject refers to a human subject between 1 and 6 years of age. In still further embodiments, a pediatric subject refers to a human subject between 6 and 12 years of age. The term "pediatric subject" may refer to infants (preterm or fullterm) and/or children, as described below.

"Infant" means a human subject ranging in age from birth to not more than one year and includes infants from 0 to 12 months corrected age. The phrase "corrected age" means an infant's chronological age minus the amount of time that the infant was born premature. Therefore, the corrected age is the age of the infant if it had been carried to full term. The term infant includes low birth weight infants, very low birth weight infants, and preterm infants. "Preterm" means an infant born before the end of the 37th week of gestation. "Full term" means an infant born after the end of the 37th week of gestation.

"Child" means a subject ranging in age from 12 months to about 13 years. In some embodiments, a child is a subject between the ages of 1 and 12 years old. In other embodiments, the terms "children" or "child" refer to subjects that are between one and about six years old, or between about seven and about 12 years old. In other embodiments, the terms "children" or "child" refer to any range of ages between 12 months and about 13 years.

"Infant formula" means a composition that satisfies at least a portion of the nutrient requirements of an infant. In the United States, the content of an infant formula is dictated by the federal regulations set forth at 21 C.F.R. Sections 100, 106, and 107.

The term "medical food" refers enteral compositions that are formulated or intended for the dietary management of a disease or disorder. A medical food may be a food for oral ingestion or tube feeding (nasogastric tube), may be labeled for the dietary management of a specific medical disorder, disease or condition for which there are distinctive nutritional requirements, and may be intended to be used under medical supervision.

The term "peptide" as used herein describes linear molecular chains of amino acids, including single chain molecules or their fragments. The peptides described herein include no more than 50 total amino acids. Peptides may further form oligomers or multimers consisting of at least two identical or different molecules. Furthermore, peptidomimetics of such peptides where amino acid(s) and/or peptide bond(s) have been replaced by functional analogs are also encompassed by the term "peptide". Such functional analogues may include, but are not limited to, all known amino acids other than the 20 gene-encoded amino acids such as selenocysteine.

The term "peptide" may also refer to naturally modified peptides where the modification is effected, for example, by glycosylation, acetylation, phosphorylation and similar modification which are well known in the art. In some embodiments, the peptide component is distinguished from a protein source also disclosed herein. Further, peptides may, for example, be produced recombinantly, semi-synthetically, synthetically, or obtained from natural sources such as after hydrolysation of proteins, including but not limited to casein, all according to methods known in the art.

The term "molar mass distribution" when used in reference to a hydrolyzed protein or protein hydrolysate pertains to the molar mass of each peptide present in the protein hydrolysate. For example, a protein hydrolysate having a molar mass distribution of greater than 500 Daltons means that each peptide included in the protein hydrolysate has a molar mass of at least 500 Daltons. Accordingly, in some embodiments, the peptides disclosed in Table 1 and Table 2 are derived from a protein hydrolysate having a molar mass distribution of greater than 500 Daltons. To produce a protein hydrolysate having a molar mass distribution of greater than 500 Daltons, a protein hydrolysate may be subjected to certain filtering procedures or any other procedure known in the art for removing peptides, amino acids, and/or other proteinaceous material having a molar mass of less than 500 Daltons. For the purposes of this disclosure, any method known in the art may be used to produce the protein hydrolysate having a molar mass distribution of greater than 500 Dalton.

The term "protein equivalent" or "protein equivalent source" includes any protein source, such as soy, egg, whey, or casein, as well as non-protein sources, such as peptides or amino acids. Further, the protein equivalent source can be any used in the art, e.g., nonfat milk, whey protein, casein, soy protein, hydrolyzed protein, peptides, amino acids, and the like. Bovine milk protein sources useful in practicing the present disclosure include, but are not limited to, milk protein powders, milk protein concentrates, milk protein isolates, nonfat milk solids, nonfat milk, nonfat dry milk, whey protein, whey protein isolates, whey protein concentrates, sweet whey, acid whey, casein, acid casein, caseinate (e.g. sodium caseinate, sodium calcium caseinate, calcium caseinate), soy bean proteins, and any combinations thereof. The protein equivalent source can, in some embodiments comprise hydrolyzed protein, including partially hydrolyzed protein and extensively hydrolyzed protein. The protein equivalent source may, in some embodiments, include intact protein. More particularly, the protein source may include a) about 20% to about 80% of the peptide component described herein, and b) about 20% to about 80% of an intact protein, a hydrolyzed protein, or a combination thereof.

The term "protein equivalent source" also encompasses free amino acids. In some embodiments, the amino acids may comprise, but are not limited to, histidine, isoleucine, leucine, lysine, methionine, cysteine, phenylalanine, tyrosine, threonine, tryptophan, valine, alanine, arginine, asparagine, aspartic acid, glutamic acid, glutamine, glycine, proline, serine, carnitine, taurine and mixtures thereof. In some embodiments, the amino acids may be branched chain amino acids. In certain other embodiments, small amino acid peptides may be included as the protein component of the nutritional composition. Such small amino acid peptides may be naturally occurring or synthesized.

"Fractionation procedure" includes any process in which a certain quantity of a mixture is divided up into a number of smaller quantities known as fractions. The fractions may be different in composition from both the mixture and other fractions. Examples of fractionation procedures include but are not limited to, melt fractionation, solvent fractionation, supercritical fluid fractionation and/or combinations thereof.

"Milk fat globule membrane" includes components found in the milk fat globule membrane including but not limited to milk fat globule membrane proteins such as Mucin 1, Butyrophilin, Adipophilin, CD36, CD14, Lactadherin (PAS6/7), Xanthine oxidase and Fatty Acid binding proteins etc. Additionally, "milk fat globule membrane" may include phospholipids, cerebrosides, gangliosides, sphingomyelins, and/or cholesterol.

The term "growing-up milk" refers to a broad category of nutritional compositions intended to be used as a part of a diverse diet in order to support the normal growth and development of a child between the ages of about 1 and about 6 years of age.

"Milk" means a component that has been drawn or extracted from the mammary gland of a mammal. In some embodiments, the nutritional composition comprises components of milk that are derived from domesticated ungulates, ruminants or other mammals or any combination thereof.

"Nutritionally complete" means a composition that may be used as the sole source of nutrition, which would supply essentially all of the required daily amounts of vitamins, minerals, and/or trace elements in combination with proteins, carbohydrates, and lipids. Indeed, "nutritionally complete" describes a nutritional composition that provides adequate amounts of carbohydrates, lipids, essential fatty acids, proteins, essential amino acids, conditionally essential amino acids, vitamins, minerals and energy required to support normal growth and development of a subject.

A nutritional composition that is "nutritionally complete" for a full term infant will, by definition, provide qualitatively and quantitatively adequate amounts of all carbohydrates, lipids, essential fatty acids, proteins, essential amino acids, conditionally essential amino acids, vitamins, minerals, and energy required for growth of the full term infant.

A nutritional composition that is "nutritionally complete" for a child will, by definition, provide qualitatively and quantitatively adequate amounts of all carbohydrates, lipids, essential fatty acids, proteins, essential amino acids, conditionally essential amino acids, vitamins, minerals, and energy required for growth of a child.

"Exogenous butyrate" or "dietary butyrate" each refer to butyrate or butyrate derivatives which are intentionally included in the nutritional composition of the present disclosure itself, rather than generated in the gut.

"Endogenous butyrate" or "butyrate from endogenous sources" each refer to butyrate present in the gut as a result of ingestion of the disclosed composition that is not added as such, but is present as a result of other components or ingredients of the composition; the presence of such other components or ingredients of the composition stimulates butyrate production in the gut.

The term "cow's milk allergy" describes a food allergy, i.e. an immune adverse reaction to one or more of the proteins contained in cow's milk in a human subject. The principal symptoms are gastrointestinal, dermatological, and respiratory symptoms. These can translate into skin rashes, hives, vomiting, diarrhea, constipation and distress. The clinical spectrum extends to diverse disorders: anaphylactic reactions, atopic dermatitis, wheeze, infantile colic, gastro esophageal reflux disease (GERD), esophagitis, colitis gastroenteritis, headache/migraine and constipation.

"Probiotic" means a microorganism with low or no pathogenicity that exerts a beneficial effect on the health of the host.

The term "non-viable probiotic" means a probiotic wherein the metabolic activity or reproductive ability of the referenced probiotic has been reduced or destroyed. More specifically, "non-viable" or "non-viable probiotic" means non-living probiotic microorganisms, their cellular components and/or metabolites thereof. Such non-viable probiotics may have been heat-killed or otherwise inactivated. The "non-viable probiotic" does, however, still retain, at the cellular level, its cell structure or other structure associated with the cell, for example exopolysaccharide and at least a portion its biological glycol-protein and DNA/RNA structure and thus retains the ability to favorably influence the health of the host. Contrariwise, the term "viable" refers to live microorganisms. As used herein, the term "non-viable" is synonymous with "inactivated".

"Prebiotic" means a non-digestible food ingredient that beneficially affects the host by selectively stimulating the growth and/or activity of one or a limited number of bacteria in the digestive tract that can improve the health of the host.

The nutritional composition of the present disclosure may be substantially free of any optional or selected ingredients described herein, provided that the remaining nutritional composition still contains all of the required ingredients or features described herein. In this context, and unless otherwise specified, the term "substantially free" means that the selected composition may contain less than a functional amount of the optional ingredient, typically less than 0.1% by weight, and also, including zero percent by weight of such optional or selected ingredient.

All percentages, parts and ratios as used herein are by weight of the total composition, unless otherwise specified.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and compositions of the present disclosure, including components thereof, can comprise, consist of, or consist essentially of the essential elements and limitations of the embodiments described herein, as well as any additional or optional ingredients, components or limitations described herein or otherwise useful in nutritional compositions.

As used herein, the term "about" should be construed to refer to both of the numbers specified as the endpoint(s) of any range. Any reference to a range should be considered as providing support for any subset within that range.

The present disclosure is directed to nutritional compositions including butyrate and LGG. Non-limiting examples of butyrate for use herein include butyric acid, butyrate salts, glycerol esters of butyric acid, and amide derivatives of amino acids, such as an acid-stable butyrate amide with the amino acid phenylalanine, such as phenylalanine-butyramide ("FBA"). Additionally, some embodiments disclosed herein may include certain butyrate derivatives as described in European Patent No. 2,268,605 to Canani et al., which is incorporated by reference herein. The nutritional compositions may further include a carbohydrate source, a protein source, and a fat or lipid source. In some embodiments, the nutritional compositions may include a component capable of stimulating endogenous butyrate production; in other embodiments, the nutritional compositions may include both dietary and endogenous butyrate.

The benefit to providing both exogenous and endogenous butyrate is accelerated tolerance acquisition towards cow's milk. Additionally, the benefit to providing both exogenous and endogenous butyrate together with *Lactobacillus* rhamnoses GG ("LGG") is accelerated tolerance acquisition toward cow's milk. Conventional dietary management of cow's milk allergy includes the use of formulations containing protein hydrolysates and amino acids rather than intact proteins. However, the inclusion of certain probiotics, such as LGG in combination with butyrate, either endogenous or exogenous butyrate, can contribute to accelerated tolerance acquisition towards cow's milk.

In some embodiments, the nutritional composition includes a source of dietary butyrate that is present in an amount of from about 5 g/100 Kcal to about 500 g/100 kcal. In some embodiments, the nutritional composition includes a source of dietary butyrate that is present in an amount of from about 15 g/100 Kcal to about 450 g/100 kcal. In some embodiments, the nutritional composition includes a source of dietary butyrate that is present in an amount of from about 20 g/100 Kcal to about 400 g/100 kcal. In some embodiments, the nutritional composition includes a source of dietary butyrate that is present in an amount of from about 25 g/100 Kcal to about 350 g/100 kcal. In some embodiments, the nutritional composition includes a source of dietary butyrate that is present in an amount of from about 30 g/100 Kcal to about 280 g/100 kcal.

In some embodiments, the nutritional composition includes from about 0.01 g to about 10 g of dietary butyrate per 100 g of total fat in the nutritional composition. In some embodiments, the nutritional composition includes from about 0.1 g to about 8 g of dietary butyrate per 100 g of total fat in the nutritional composition. In some embodiments, the nutritional composition includes from about 0.4 g to about 7 g of dietary butyrate per 100 g of total fat in the nutritional composition. In some embodiments, the nutritional composition includes from about 0.7 g to about 6.5 g of dietary butyrate per 100 g of total fat in the nutritional composition. In some embodiments, the nutritional composition includes from about 1.2 g to about 5.1 g of dietary butyrate per 100 g of total fat in the nutritional composition.

In some embodiments the dietary butyrate is provided by one or more of the following: butyric acid; butyrate salts, including sodium butyrate, potassium butyrate, calcium butyrate, and/or magnesium butyrate; glycerol esters of butyric acid; and/or amide derivative of butyric acid. In some embodiments, the dietary butyrate is one or more of the following: N-(1-carbamoyl-2-phenyl-ethyl) butyramide; N-(1-butyroyl-carbamoyl-2-phenyl-ethyl)butyramide; 5-benzyl-2-propyl-1H-imidazol-4(5H)-one; N-(1-oxo-3-phenyl-1-(piperidin-1-yl)propan-2-yl)butyramide; N-(1-oxo-3-phenyl-1-(pyrrolidin-1-yl)propan-2-yl)butyramide; N-(1-(methylcarbamoyl)-2-phenylethyl) butyramide; N-(1-(ethylcarbamoyl)-2-phenylethyl)butyramide; N-(1-(propylcarbamoyl)-2-phenylethyl)butyramide; N-(1-(butylcarbamoyl)-2-phenylethyl)butyramide; N-(1-(pentylcarbamoyl)-2-phenylethyl)butyramide; N-(1-carbamoyl-2-phenylethyl)-N-methyl butyramide; N-(1-carbamoyl-2-phenylethyl)-N-ethylbutyramide; N-(1-carbamoyl-2-phenylethyl)-N-propylbutyramide; and/or corresponding mixtures and corresponding salts of pharmaceutically acceptable bases or acids, pure diastereoisomeric forms and enantiomeric forms or mixtures thereof.

The dietary butyrate can be supplied by any suitable source known in the art. Non-limiting sources of dietary butyrate includes animal source fats and derived products, such as but not limited to milk, milk fat, butter, buttermilk, butter serum, cream; microbial fermentation derived products, such as but not limited to yogurt and fermented buttermilk; and plant source derived seed oil products, such as pineapple and/or pineapple oil, apricot and/or apricot oil, barley, oats, brown rice, bran, green beans, legumes, leafy greens, apples, kiwi, oranges. In some embodiments, the dietary butyrate is synthetically produced. In embodiments where the dietary butyrate is synthetically produced, the chemical structure of the dietary butyrate may be modified as necessary. Further, the dietary butyrate produced synthetically can be purified by any means known in the art to produce a purified dietary butyrate additive that can be incorporated into the nutritional compositions disclosed herein. The dietary butyrate may be provided by dairy lipids and/or triglyceride bound forms of butyrate.

In some embodiments, the dietary butyrate may be provided in an encapsulated form. In certain embodiments, the encapsulation of the dietary butyrate may provide for longer shelf-stability and may provide for improved organoleptic properties of the nutritional composition. For example, in some embodiments, the dietary butyrate may be encapsulated or coated by the use of, or combination of, fat derived materials, such as mono- and di-glycerides; sugar and acid esters of glycerides; phospholipids; plant, animal and microbial derived proteins and hydrocolloids, such as starches, maltodextrins, gelatin, pectins, glucans, caseins, soy proteins, and/or whey proteins.

The dietary butyric acid may also be provided in a coated form. For example, coating certain glycerol esters of butyric acids and/or amide derivatives of butyric acids with fat derived materials, such as mono- and di-glycerides; sugar and acid esters of glycerides; phospholipids; plant, animal and microbial derived proteins and hydrocolloids, such as starches, maltodextrins, gelatin, pectins, glucans, caseins, soy proteins, and/or whey proteins may improve the shelf-stability of the dietary butyrate and may further improve the overall organoleptic properties of the nutritional composition.

In certain embodiments, the dietary butyrate comprises alkyl, and or glycerol esters of butyric acid. Glycerol esters of butyric acid may offer minimal complexity when formulated and processed in the nutritional composition. Additionally, glycerol esters of butyric acid may improve the shelf life of the nutritional composition including dietary butyrate an may further have a low impact on the sensory attributes of the finished product.

The dietary butyrate comprises amide derivatives of butyric acid in some embodiments. Generally, these amide derivatives of butyric acid are a solid, odorless, and tasteless form and are more stable than certain butyric acid esters at gastric pH. Further, the amide derivatives of butyric acid are able to release the corresponding acid by alkaline hydrolysis in the small and large intestine, thereby allowing for absorption of the dietary butyrate.

In certain embodiments, the dietary butyrate comprises a phenylalanine amide derivative of butyric acid. Furthermore, use of a phenylalanine amide derivative of butyric acid provides for improved organoleptic and physicochemical characteristics as it is an odorless and colorless solid crystalline powder. Furthermore, the purification of phenylalanine amide derivatives of butyric acid may be particularly economical for purification in terms of the cost to purify versus the yield of compound ratio. Accordingly, in certain embodiments, the dietary butyrate may comprise an acid-stable butyrate amide with the amino acid phenylalanine, such as phenylalanine-butyramide ("FBA"). FBA is stable to acids and alkalis and, thus, is able to release butyric acid in the small and large intestine in a constant manner over time. Furthermore, FBA does not have the unpleasant odor of butyrate and is practically tasteless, thus overcoming the main limitation of the use of butyrate, namely its poor palatability. Moreover, the solubility of FBA in water is satisfactory as it produces clear solutions up to the concentration 0.1 M and suspensions at higher concentrations. Accordingly, FBA is a suitable form of dietary butyrate that may be incorporated into powdered nutritional compositions that are to be reconstituted with water or some other type of liquid.

In further embodiments, the amide derivative of butyric acid with phenylalanine, or suitable derivatives of the latter, is prepared by reacting the appropriate phenylalanine derivative with butyroyl chloride, or an equivalent derivative of butyric acid (simple or mixed ester or anhydride) in an aprotic polar inert organic solvent, at room temperature. Following this reaction the monobutyroyl derivative is formed, which is the main component in quantitative terms, accompanied, according to the structure of the starting products, also by the dibutyroyl derivative of the initial phenylalanine compound and other derivatives, resulting, for example, from the cyclisation of the main product during the reaction.

In some embodiments, the amide derivative of butyric acid with phenylalanine may be isolated and/or purified by the means of known techniques. However, in certain embodiments the amide derivative of butyric acid with phenylalanine can be advantageously incorporated into a suitable nutritional composition without prior separation into the individual constituent components and, in this state, the amide derivative of butyric acid with phenylalanine has the desired physicochemical, organoleptic, and pharmacokinetic properties.

In some embodiments, the dietary butyrate comprises an amide derivative of a short chain fatty acid obtainable by the reaction of a derivative of said fatty acid with a phenylalanine derivative according to the following general formula:

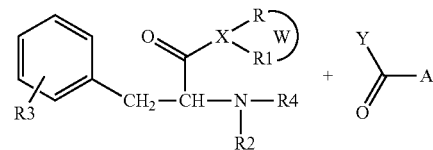

wherein: Y represents an atom of halogen, alkoxyl (2-6 carbon atoms), acyl (2-6 carbon atoms); A represents a straight or branched C(1-5) alkyl chain, possibly substituted with phenyl; X represents oxygen, nitrogen or sulphur, with the proviso that: when X represents oxygen or sulphur, R represents hydrogen or a (C1-6) alkyl group, and R1 and W are nil and/or when X represents nitrogen, R and R1 independently represent, hydrogen or a (C1-6 alkyl group or a (C1-6 acyl group and W is nil; or W represents a 1,2-alkylene chain with 2 to 6 carbon atoms and R and R1 are methylene groups; R2 and R4 independently represent, hydrogen or a (C1-6 alkyl group or a (C1-6 acyl group; R3 is selected from the group consisting of H, (C1-6)alkyl, (C1-6)alkoxyl, halogen, oxidryl, cyano, nitro, amino, mono- or di-(C1-6) alkyl amino (C2-6) acylamino, formyl, hydroxyiminomethyl, (C1-6)alkoxyiminomethyl and carbamoyl. Further, in certain embodiments, the derivatives according to the present disclosure include their salts with pharmaceutically acceptable bases or acids and their possible diastereoisomeric and enantiomeric forms.

In certain embodiments, the dietary butyrate may include an amide derivative of a short chain fatty acid having the following general formula:

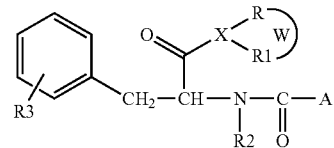

wherein A, X, W, R, $R_1$, $R_2$, and $R_3$ have the same meanings as indicated above, and the corresponding salts with pharmaceutically acceptable bases, as well as the possible diastereoisomeric and enantiomeric forms.

In some embodiments, the dietary butyrate may comprise a mixture of amide derivatives of butyric acid. For example, in some embodiments the dietary butyrate may comprise one or more of the following three compounds:

N-(1-carbamoyl-2-phenyl-ethyl)butyramide, of formula:

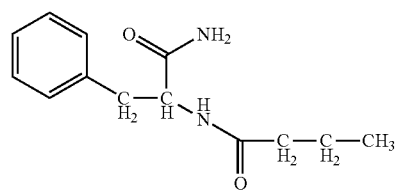 [SMILES: CCCC(=O)NC(Cc1ccccc1)C(N)=O]

N-(1-butyroyl-carbamoyl-2-phenyl-ethyl)butyramide, of formula:

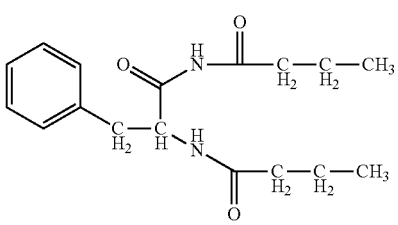 [SMILES: CCCC(=O)NC(=O)C(Cc1ccccc1)NC(=O)CCC]

5-benzyl-2-propyl-1H-imidazol-4(5H)-one, of formula:

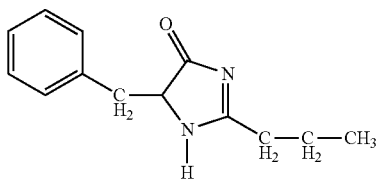 [SMILES: CCCC1=NC(=O)C(Cc2ccccc2)N1]

In certain embodiments, these compounds can be used in mixtures or may be isolated and purified according to techniques known in the art. In certain embodiments, the amide derivatives provided above may be isolated as free forms and/or as the corresponding salts of pharmaceutically acceptable bases or acids. In certain embodiments, the pharmaceutically acceptable salts may include sodium and potassium salts, ammonium salts, ethylenediamine and aliphatic or aromatic nitrogen bases, hydrochlorides, sulphates, aliphatic or aromatic acids. Furthermore, these compounds may exist as racemic forms or as possible diastereoisomer forms that can be obtained by procedures known in the art.

In some embodiments, dietary butyrate may comprise butyric acid amide derivatives using other amino acids, for example, tyrosine and/or histidine. In some embodiments, any suitable amino acid known in the art may be utilized in preparing the butyric acid amide derivative used as a source of dietary butyrate. Without being bound by any particular theory, it is believed that dietary butyrate comprised of butyric acid amide derivatives may resist the action of gastric acids and the processing conditions encountered in nutritional composition, such as infant formula, manufacturing. Accordingly, in embodiments where the dietary butyrate is provided by one or more butyric acid amide derivatives the resulting nutritional composition includes a stable dietary butyrate formulation with improved organoleptic properties.

In some embodiments, the dietary butyrate may comprise butyrate salts, for example, sodium butyrate, potassium butyrate, calcium butyrate, magnesium butyrate, and combinations thereof. In some embodiments, the use of selected dietary butyrate salts may improve intestinal health when provided to target subjects. In certain embodiments, dietary butyrate comprises a suitable butyrate salt that has been coated with one or more fats or lipids. In certain embodiments wherein the dietary butyrate comprises a fat coated butyrate salt, the nutritional composition may be a dry-powdered composition into which the dietary butyrate is incorporated.

In some embodiments, the dietary butyrate may comprise any of the butyrate compounds disclosed herein that are formulated to be in complex form with chitosan or one or cyclodextrins. For example, cyclodextrins are cyclic oligosaccharides composed of six (α-cyclodextrin), seven (β-cyclodextrin), or eight (gamma-cyclodextrin) units of α-1,4-glucopyranose. Cyclodextrins are further characterized by a hydrophilic exterior surface and a hydrophobic core. Without being bound by any particular theory, the aliphatic butyrate chain would form a complex with the cyclodextrin core, thus increasing its molecular weight and, thus, reducing the volatility of the butyrate compound. Accordingly, the bioavailability of dietary butyrate may be improved when the dietary butyrate includes butyrate compounds in complex form with one or more cyclodextrins. Further, cyclodextrins are bulky hydrophobic molecules that are resistant to stomach acid as well as gastrointestinal enzymes, thus administration of the butyrate-cyclodextrin complex as described herein would promote absorption of the dietary butyrate in the small intestines.

In some embodiments the dietary butyrate is provided from an enriched lipid fraction derived from milk. For example, bovine milk fat has a butyric acid content that may be 20 times higher than the butyric acid content in human milk fat. Furthermore, among the short chain fatty acids ("SCFAs") present in human milk, i.e. fatty acids having a carbon chain length from 4 to 12, butyric acid (C4) is one of the most predominant in bovine milk. As such, bovine milk fat and/or enriched fractions of bovine milk fat may be included in a nutritional composition to provide dietary butyrate.

In embodiments where the dietary butyrate is provided by an enriched lipid fraction derived from milk the enriched lipid fraction derived from milk may be produced by any number of fractionation techniques. These techniques include but are not limited to melting point fractionation, organic solvent fractionation, super critical fluid fractionation, and any variants and combinations thereof.

Furthermore, mixtures that may be subjected to the fractionation procedures to produce the enriched lipid fraction include, but are not limited to, bovine whole milk, bovine cream, caprine milk, ovine milk, yak milk, and/or mixtures thereof. In a preferred embodiment the milk mixture used to create the enriched lipid fraction is bovine milk.

In addition to providing dietary butyrate, the enriched lipid fraction may comprise an one of the following ingredients: saturated fatty acids; trans-fatty acids; branched-chain fatty acids ("BCFAs"), including odd-branched chain fatty acids ("OBCFAs"); conjugated linoleic acid ("CLA"); monounsaturated fatty acids; polyunsaturated fatty acids; cholesterol; phospholipids; and milk fat globule membrane, including milk fat globule membrane protein.

In some embodiments the enriched lipid fraction includes, per 100 Kcal, one or more of the following:
from about 0.1 g to 8.0 g of saturated fatty acids;
from about 0.2 g to 7.0 g trans-fatty acids;
from about 0.003 g to about 6.1 g branched-chain fatty acids;
from about 0.026 g to about 2.5 g conjugated linoleic acid;
from about 0.8 g to about 2.5 g monounsaturated fatty acids;
from about 2.3 g to about 4.4 g polyunsaturated fatty acids;
from about 100 mg to about 400 mg of cholesterol;
from about 50 mg to about 400 mg of phospholipids; and/or
from about 10 mg to about 500 mg of milk fat globule membrane.

The following example illustrates a milk fat fraction having an enriched concentration of butyric acid (C4) that may be produced by a fractionation procedure.

EXAMPLE 1

Illustrated below is a lipid profile of fractionated milk fat produced by super critical carbon extraction fractionation procedure and by melt-fractionation.

Milk Fat composition (g fatty acid/100 g TOTAL fatty acids)

|  | AMF | SCCO2 | MeltFrac 10C |
|---|---|---|---|
| C 4:0 | 3.9 | 6.0 | 4.7 |
| C 6:0 | 2.5 | 3.3 | 2.9 |
| C 8:0 | 1.4 | 1.9 | 1.8 |
| C 10:0 | 3.1 | 3.9 | 3.8 |
| C 12:0 | 4.2 | 4.1 | 4.8 |
| C 14:0 | 11.4 | 12.2 | 10.9 |
| C 14:1 | 1.1 | 1.0 | 1.3 |
| C 15:0 | 1.1 | 1.0 | 0.9 |
| C 16:0 | 29.4 | 29.6 | 22.3 |
| C 16:1 | 1.9 | 1.4 | 2.2 |
| C 17:0 | 0.6 | 0.5 | 0.4 |
| C 18:0 | 11.4 | 8.2 | 6.1 |
| C 18:1, cis, ω9 | 21.9 | 16.5 | 25.3 |
| C 18:1, trans, ω9 | 0.3 | 1.6 | 1.9 |
| C 18:2, ω 6 | 1.9 | 2.2 | 1.9 |
| C 18:3, ω 3, a | 0.6 | 0.4 | 0.6 |
| C 20:0 | 0.0 | 0.1 | 0.1 |
| C 20:1, ω 9 | 0.1 | 0.1 | 0.2 |
| Saturated | 68.7 | 70.7 | 58.6 |
| Unsaturated | 27.8 | 23.1 | 33.3 |

AMF=anhydrous milk fat; SCCO2=super-critical carbon dioxide fraction (super olein).

MeltFrac=melt crystallization fraction separated at 10° C.

The nutritional composition of the present disclosure also includes at least one probiotic; in a preferred embodiment, the probiotic comprises LGG. In certain other embodiments, the probiotic may be selected from any other *Lactobacillus* species, *Bifidobacterium* species, *Bifidobacterium longum* BB536 (BL999, ATCC: BAA-999), *Bifidobacterium longum* AH1206 (NCIMB: 41382), *Bifidobacterium breve* AH1205 (NCIMB: 41387), *Bifidobacterium infantis* 35624 (NCIMB: 41003), and *Bifidobacterium animalis* subsp. *lactis* BB-12 (DSM No. 10140) or any combination thereof.

The amount of the probiotic may vary from about $1 \times 10^4$ to about $1.5 \times 10^{12}$ cfu of probiotic(s) per 100 kcal. In some embodiments the amount of probiotic may be from about $1 \times 10^6$ to about $1 \times 10^9$ cfu of probiotic(s) per 100 kcal. In certain other embodiments the amount of probiotic may vary from about $1 \times 10^7$ cfu/100 kcal to about $1 \times 10^8$ cfu of probiotic(s) per 100 kcal.

As noted, in a preferred embodiment, the probiotic comprises LGG. LGG is a probiotic strain isolated from healthy human intestinal flora. It was disclosed in U.S. Pat. No. 5,032,399 to Gorbach, et al., which is herein incorporated in its entirety, by reference thereto. LGG is resistant to most antibiotics, stable in the presence of acid and bile, and attaches avidly to mucosal cells of the human intestinal tract. It survives for 1-3 days in most individuals and up to 7 days in 30% of subjects. In addition to its colonization ability, LGG also beneficially affects mucosal immune responses. LGG is deposited with the depository authority American Type Culture Collection ("ATCC") under accession number ATCC 53103.

In an embodiment, the probiotic(s) may be viable or non-viable. The probiotics useful in the present disclosure may be naturally-occurring, synthetic or developed through the genetic manipulation of organisms, whether such source is now known or later developed.

In some embodiments, the nutritional composition may include a source comprising probiotic cell equivalents, which refers to the level of non-viable, non-replicating probiotics equivalent to an equal number of viable cells. The term "non-replicating" is to be understood as the amount of non-replicating microorganisms obtained from the same amount of replicating bacteria (cfu/g), including inactivated probiotics, fragments of DNA, cell wall or cytoplasmic compounds. In other words, the quantity of non-living, non-replicating organisms is expressed in terms of cfu as if all the microorganisms were alive, regardless whether they are dead, non-replicating, inactivated, fragmented etc. In non-viable probiotics are included in the nutritional composition, the amount of the probiotic cell equivalents may vary from about $1 \times 10^4$ to about $1.5 \times 10^{10}$ cell equivalents of probiotic(s) per 100 kcal. In some embodiments the amount of probiotic cell equivalents may be from about $1 \times 10^6$ to about $1 \times 10^9$ cell equivalents of probiotic(s) per 100 kcal nutritional composition. In certain other embodiments the amount of probiotic cell equivalents may vary from about $1 \times 10^7$ to about $1 \times 10^8$ cell equivalents of probiotic(s) per 100 kcal of nutritional composition.

In some embodiments, the probiotic source incorporated into the nutritional composition may comprise both viable colony-forming units, and non-viable cell-equivalents.

While, probiotics may be helpful in pediatric patients, the administration of viable bacteria to pediatric subjects, and particularly preterm infants, with impaired intestinal defenses and immature gut barrier function may not be feasible due to the risk of bacteremia. Therefore, there is a need for compositions that can provide the benefits of probiotics without introducing viable bacteria into the intestinal tract of pediatric subjects While not wishing to be bound by theory, it is believed that a culture supernatant from batch cultivation of a probiotic, and in particular embodiments, LGG, provides beneficial gastrointestinal benefits. It is further believed that the beneficial effects on gut barrier function can be attributed to the mixture of components (including proteinaceous materials, and possibly including (exo)polysaccharide materials) that are released into the culture medium at a late stage of the exponential (or "log") phase of batch cultivation of LGG. The composition will be hereinafter referred to as "culture supernatant."

Accordingly, in some embodiments, the nutritional composition includes a culture supernatant from a late-exponential growth phase of a probiotic batch-cultivation process. Without wishing to be bound by theory, it is believed that the activity of the culture supernatant can be attributed to the mixture of components (including proteinaceous materials, and possibly including (exo)polysaccharide materials) as found released into the culture medium at a late stage of the exponential (or "log") phase of batch cultivation of the probiotic. The term "culture supernatant" as used herein, includes the mixture of components found in the culture medium. The stages recognized in batch cultivation of bacteria are known to the skilled person. These are the "lag," the "log" ("logarithmic" or "exponential"), the "stationary" and the "death" (or "logarithmic decline") phases. In all phases during which live bacteria are present, the bacteria metabolize nutrients from the media, and secrete (exert, release) materials into the culture medium. The composition of the secreted material at a given point in time of the growth stages is not generally predictable.

In an embodiment, a culture supernatant is obtainable by a process comprising the steps of (a) subjecting a probiotic such as LGG to cultivation in a suitable culture medium using a batch process; (b) harvesting the culture supernatant at a late exponential growth phase of the cultivation step, which phase is defined with reference to the second half of the time between the lag phase and the stationary phase of the batch-cultivation process; (c) optionally removing low molecular weight constituents from the supernatant so as to retain molecular weight constituents above 5-6 kiloDaltons (kDa); (d) removing liquid contents from the culture supernatant so as to obtain the composition.

The culture supernatant may comprise secreted materials that are harvested from a late exponential phase. The late exponential phase occurs in time after the mid exponential phase (which is halftime of the duration of the exponential phase, hence the reference to the late exponential phase as being the second half of the time between the lag phase and the stationary phase). In particular, the term "late exponential phase" is used herein with reference to the latter quarter portion of the time between the lag phase and the stationary phase of the LGG batch-cultivation process. In some embodiments, the culture supernatant is harvested at a point in time of 75% to 85% of the duration of the exponential phase, and may be harvested at about ⅚ of the time elapsed in the exponential phase.

The culture supernatant is believed to contain a mixture of amino acids, oligo- and polypeptides, and proteins, of various molecular weights. The composition is further believed to contain polysaccharide structures and/or nucleotides.

In some embodiments, the culture supernatant of the present disclosure excludes low molecular weight components, generally below 6 kDa, or even below 5 kDa. In these and other embodiments, the culture supernatant does not include lactic acid and/or lactate salts. These lower molecular weight components can be removed, for example, by filtration or column chromatography.

The culture supernatant of the present disclosure can be formulated in various ways for administration to pediatric subjects. For example, the culture supernatant can be used as such, e.g. incorporated into capsules for oral administration, or in a liquid nutritional composition such as a drink, or it can be processed before further use. Such processing generally involves separating the compounds from the generally liquid continuous phase of the supernatant. This preferably is done by a drying method, such as spray-drying or freeze-drying (lyophilization). Spray-drying is preferred. In a preferred embodiment of the spray-drying method, a carrier material will be added before spray-drying, e.g., maltodextrin DE29.

The LGG culture supernatant of the present disclosure, whether added in a separate dosage form or via a nutritional product, will generally be administered in an amount effective in promoting gut regeneration, promoting gut maturation and/or protecting gut barrier function. The effective amount is preferably equivalent to $1\times10^4$ to about $1\times10^{12}$ cell equivalents of live probiotic bacteria per kg body weight per day, and more preferably $10^8$-$10^9$ cell equivalents per kg body weight per day. In other embodiments, the amount of cell equivalents may vary from about $1\times10^4$ to about $1.5\times10^{10}$ cell equivalents of probiotic(s) per 100 Kcal. In some embodiments the amount of probiotic cell equivalents may be from about $1\times10^6$ to about $1\times10^9$ cell equivalents of probiotic(s) per 100 Kcal nutritional composition. In certain other embodiments the amount of probiotic cell equivalents may vary from about $1\times10^7$ to about $1\times10^8$ cell equivalents of probiotic(s) per 100 Kcal of nutritional composition.

Without being bound by any theory, it is believed the disclosed combination of dietary butyrate and probiotic, especially LGG, provides a higher potential to bring allergic infants and children to a normal diet, fast management of CMA manifestations, and can accelerate the development of tolerance acquisition in infants affected by CMA. The unique combination of nutrients in the disclosed nutritional composition(s) is believed to be capable of providing novel and unexpected benefits for infants and children. Moreover, the benefit of this nutritional composition is believed to be obtained during infancy, and also by including it as part of a diverse diet as the child continues to grow and develop.

In an embodiment, the nutritional composition further comprises a component for stimulating endogenous butyrate production. For example, in some embodiments the component for stimulating endogenous butyrate production comprises a microbiota-stimulating component that is a prebiotic including both polydextrose ("PDX") and galacto-oligosaccharides ("GOS"). A prebiotic component including PDX and GOS can enhance butyrate production by microbiota. Butyrate has epigenetic (histone deacetylase inhibition activity) that results in regulatory responses such as generation of regulatory T-cells. In the context of cow s milk allergy, these regulatory responses may result in accelerated tolerance acquisition to cow's milk protein.

In addition to PDX and GOS, the nutritional composition may also contain one or more other prebiotics which can exert additional health benefits, which may include, but are not limited to, selective stimulation of the growth and/or activity of one or a limited number of beneficial gut bacteria, stimulation of the growth and/or activity of ingested probiotic microorganisms, selective reduction in gut pathogens, and favorable influence on gut short chain fatty acid profile. Such prebiotics may be naturally-occurring, synthetic, or developed through the genetic manipulation of organisms and/or plants, whether such new source is now known or developed later. Prebiotics useful in the present disclosure may include oligosaccharides, polysaccharides, and other prebiotics that contain fructose, xylose, soya, galactose, glucose and mannose.

More specifically, prebiotics useful in the present disclosure include PDX and GOS, and can, in some embodiments, also include, PDX powder, lactulose, lactosucrose, raffinose, gluco-oligosaccharide, inulin, fructo-oligosaccharide (FOS), isomalto-oligosaccharide, soybean oligosaccharides, lactosucrose, xylo-oligosaccharide (XOS), chito-oligosaccharide, manno-oligosaccharide, aribino-oligosaccharide, siallyl-oligosaccharide, fuco-oligosaccharide, and gentio-oligosaccharides.

In an embodiment, the total amount of prebiotics present in the nutritional composition may be from about 1.0 g/L to about 10.0 g/L of the composition. More preferably, the total amount of prebiotics present in the nutritional composition may be from about 2.0 g/L and about 8.0 g/L of the composition. In some embodiments, the total amount of prebiotics present in the nutritional composition may be from about 0.01 g/100 Kcal to about 1.5 g/100 Kcal. In certain embodiments, the total amount of prebiotics present in the nutritional composition may be from about 0.15 g/100 Kcal to about 1.5 g/100 Kcal. In some embodiments, the prebiotic component comprises at least 20% w/w PDX and GOS.

The amount of PDX in the nutritional composition may, in an embodiment, be within the range of from about 0.015 g/100 Kcal to about 1.5 g/100 Kcal. In another embodiment, the amount of polydextrose is within the range of from about 0.2 g/100 Kcal to about 0.6 g/100 Kcal. In some embodiments, PDX may be included in the nutritional composition in an amount sufficient to provide between about 1.0 g/L and 10.0 g/L. In another embodiment, the nutritional composition contains an amount of PDX that is between about 2.0 g/L and 8.0 g/L. And in still other embodiments, the amount of PDX in the nutritional composition may be from about 0.05 g/100 Kcal to about 1.5 g/100 Kcal.

The prebiotic component also comprises GOS. The amount of GOS in the nutritional composition may, in an embodiment, be from about 0.015 g/100 Kcal to about 1.0 g/100 Kcal. In another embodiment, the amount of GOS in the nutritional composition may be from about 0.2 g/100 Kcal to about 0.5 g/100 Kcal.

In a particular embodiment, GOS and PDX are supplemented into the nutritional composition in a total amount of at least about 0.015 g/100 Kcal or about 0.015 g/100 Kcal to about 1.5 g/100 Kcal. In some embodiments, the nutritional composition may comprise GOS and PDX in a total amount of from about 0.1 to about 1.0 g/100 Kcal.

In certain embodiments, the PDX- and GOS-containing prebiotic and dietary butyrate is incorporated into a nutritional composition that is an infant formula. Currently, many infant formulas are not formulated with dietary butyrate. One reason that infant formulas include little to no dietary butyrate is due to the unpleasant organoleptic properties exhibited by the nutritional composition when butyrate compounds are incorporated into the nutritional composition. For example, many butyrate compounds exhibit an odor that makes consuming the nutritional composition in which they are incorporated an unpleasant experience. Furthermore, the pediatric and infant population will not readily consume nutritional products having an unpleasant odor, taste, and/or mouthfeel. Accordingly, there exists a need for a nutritional composition formulated for administration to a pediatric subject or an infant that provides butyrate in the gut yet does not have diminished organoleptic properties. The incorporation of a prebiotic to stimulate butyrate production by gut microbiota and certain dietary butyrate compounds disclosed herein, i.e. glycerol esters of butyric acid and amide derivatives of amino acids, into pediatric and infant nutritional compositions will provide butyrate while still providing a pleasant sensory experience.

In some embodiments, the nutritional composition includes a protein equivalent source, wherein the protein equivalent source includes a peptide component comprising SEQ ID NO 4, SEQ ID NO 13, SEQ ID NO 17, SEQ ID NO 21, SEQ ID NO 24, SEQ ID NO 30, SEQ ID NO 31, SEQ ID NO 32, SEQ ID NO 51, SEQ ID NO 57, SEQ ID NO 60, and SEQ ID NO 63. In some embodiments, the peptide component may comprise additional peptides disclosed in Table 1. For example, the composition may include at least 10 additional peptides disclosed in Table 1. In some embodiments, 20% to 80% of the protein equivalent source comprises the peptide component, and 20% to 80% of the protein equivalent source comprises an intact protein, a partially hydrolyzed protein, and combinations thereof. In some embodiments, the term additional means selecting different peptides than those enumerated.

In another embodiment, 1% to about 99% of the protein equivalent source includes a peptide component comprising at least 3 peptides selected from the group consisting of SEQ ID NO 4, SEQ ID NO 13, SEQ ID NO 17, SEQ ID NO 21, SEQ ID NO 24, SEQ ID NO 30, SEQ ID NO 31, SEQ ID NO 32, SEQ ID NO 51, SEQ ID NO 57, SEQ ID NO 60, and SEQ ID NO 63, and at least 5 additional peptides selected from Table 1; and wherein 1% to 99% of the protein equivalent source comprises an intact protein, a partially hydrolyzed protein, or combinations thereof. In some embodiments, 20% to 80% of the protein equivalent source includes a peptide component comprising at least 3 peptides selected from the group consisting of SEQ ID NO 4, SEQ ID NO 13, SEQ ID NO 17, SEQ ID NO 21, SEQ ID NO 24, SEQ ID NO 30, SEQ ID NO 31, SEQ ID NO 32, SEQ ID NO 51, SEQ ID NO 57, SEQ ID NO 60, and SEQ ID NO 63, and at least 5 additional peptides selected from Table 1; and wherein 20% to 80% of the protein equivalent source comprises an intact protein, a partially hydrolyzed protein, or combinations thereof.

Table 1 below identifies the amino acid sequences of the peptides that may be included in the peptide component of the present nutritional compositions.

TABLE 1

| Seq. ID | Amino Acid Sequence | | | | | | | | (aa) |
|---|---|---|---|---|---|---|---|---|---|
| 1 | Ala | Ile | Asn | Pro | Ser | Lys | Glu | Asn | 8 |
| 2 | Ala | Pro | Phe | Pro | Glu | | | | 5 |
| 3 | Asp | Ile | Gly | Ser | Glu | Ser | | | 6 |
| 4 | Asp | Lys | Thr | Glu | Ile | Pro | Thr | | 7 |
| 5 | Asp | Met | Glu | Ser | Thr | | | | 5 |
| 6 | Asp | Met | Pro | Ile | | | | | 4 |
| 7 | Asp | Val | Pro | Ser | | | | | 4 |
| n/a | Glu | Asp | Ile | | | | | | 3 |
| n/a | Glu | Leu | Phe | | | | | | 3 |
| n/a | Glu | Met | Pro | | | | | | 3 |
| 8 | Glu | Thr | Ala | Pro | Val | Pro | Leu | | 7 |
| 9 | Phe | Pro | Gly | Pro | Ile | Pro | | | 6 |
| 10 | Phe | Pro | Gly | Pro | Ile | Pro | Asn | | 7 |
| 11 | Gly | Pro | Phe | Pro | | | | | 4 |
| 12 | Gly | Pro | Ile | Val | | | | | 4 |
| 13 | Ile | Gly | Ser | Glu | Ser | Thr | Glu | Asp | Gln | 9 |
| 14 | Ile | Gly | Ser | Ser | Ser | Glu | Glu | Ser | | 8 |
| 15 | Ile | Gly | Ser | Ser | Ser | Glu | Glu | Ser | Ala | 9 |
| 16 | Ile | Asn | Pro | Ser | Lys | Glu | | | | 6 |
| 17 | Ile | Pro | Asn | Pro | Ile | | | | | 5 |
| 18 | Ile | Pro | Asn | Pro | Ile | Gly | | | | 6 |
| 19 | Ile | Pro | Pro | Leu | Thr | Gln | Thr | Pro | Val | 9 |
| 20 | Ile | Thr | Ala | Pro | | | | | | 4 |
| 21 | Ile | Val | Pro | Asn | | | | | | 4 |
| 22 | Lys | His | Gln | Gly | Leu | Pro | Gln | | | 7 |
| 23 | Leu | Asp | Val | Thr | Pro | | | | | 5 |
| 24 | Leu | Glu | Asp | Ser | Pro | Glu | | | | 6 |
| 25 | Leu | Pro | Leu | Pro | Leu | | | | | 5 |

TABLE 1-continued

| Seq. ID | Amino Acid Sequence | | | | | | | | | | (aa) |
|---|---|---|---|---|---|---|---|---|---|---|---|
| 26 | Met | Glu | Ser | Thr | Glu | Val | | | | | 6 |
| 27 | Met | His | Gln | Pro | His | Gln | Pro | Leu | Pro | Pro | Thr | 11 |
| 28 | Asn | Ala | Val | Pro | Ile | | | | | | 5 |
| 29 | Asn | Glu | Val | Glu | Ala | | | | | | 5 |
| n/a | Asn | Leu | Leu | | | | | | | | 3 |
| 30 | Asn | Gln | Glu | Gln | Pro | Ile | | | | | 6 |
| 31 | Asn | Val | Pro | Gly | Glu | | | | | | 5 |
| 32 | Pro | Phe | Pro | Gly | Pro | Ile | | | | | 6 |
| 33 | Pro | Gly | Pro | Ile | Pro | Asn | | | | | 6 |
| 34 | Pro | His | Gln | Pro | Leu | Pro | Pro | Thr | | | 8 |
| 35 | Pro | Ile | Thr | Pro | Thr | | | | | | 5 |
| 36 | Pro | Asn | Pro | Ile | | | | | | | 4 |
| 37 | Pro | Asn | Ser | Leu | Pro | Gln | | | | | 6 |
| 38 | Pro | Gln | Leu | Glu | Ile | Val | Pro | Asn | | | 8 |
| 39 | Pro | Gln | Asn | Ile | Pro | Pro | Leu | | | | 7 |
| 40 | Pro | Val | Leu | Gly | Pro | Val | | | | | 6 |
| 41 | Pro | Val | Pro | Gln | | | | | | | 4 |
| 42 | Pro | Val | Val | Val | Pro | | | | | | 5 |
| 43 | Pro | Val | Val | Val | Pro | Pro | | | | | 6 |
| 44 | Ser | Ile | Gly | Ser | Ser | Ser | Glu | Glu | Ser | Ala | Glu | 11 |
| 45 | Ser | Ile | Ser | Ser | Ser | Glu | Glu | | | | 7 |
| 46 | Ser | Ile | Ser | Ser | Ser | Glu | Glu | Ile | Val | Pro | Asn | 11 |
| 47 | Ser | Lys | Asp | Ile | Gly | Ser | Glu | | | | 7 |
| 48 | Ser | Pro | Pro | Glu | Ile | Asn | | | | | 6 |
| 49 | Ser | Pro | Pro | Glu | Ile | Asn | Thr | | | | 7 |
| 50 | Thr | Asp | Ala | Pro | Ser | Phe | Ser | | | | 7 |
| 51 | Thr | Glu | Asp | Glu | Leu | | | | | | 5 |
| 52 | Val | Ala | Thr | Glu | Glu | Val | | | | | 6 |
| 53 | Val | Leu | Pro | Val | Pro | | | | | | 5 |
| 54 | Val | Pro | Gly | Glu | | | | | | | 4 |
| 55 | Val | Pro | Gly | Glu | Ile | Val | | | | | 6 |
| 56 | Val | Pro | Ile | Thr | Pro | Thr | | | | | 6 |
| 57 | Val | Pro | Ser | Glu | | | | | | | 4 |
| 58 | Val | Val | Pro | Pro | Phe | Leu | Gln | Pro | Glu | | 9 |
| 59 | Val | Val | Val | Pro | Pro | | | | | | 5 |
| 60 | Tyr | Pro | Phe | Pro | Gly | Pro | | | | | 6 |
| 61 | Tyr | Pro | Phe | Pro | Gly | Pro | Ile | Pro | | | 8 |
| 62 | Tyr | Pro | Phe | Pro | Gly | Pro | Ile | Pro | Asn | | 9 |
| 63 | Tyr | Pro | Ser | Gly | Ala | | | | | | 5 |
| 64 | Tyr | Pro | Val | Glu | Pro | | | | | | 5 |

Table 2 below further identifies a subset of amino acid sequences from Table 1 that may be included in the peptide component disclosed herein.

TABLE 2

| Seq ID Number | Amino Acid Sequence | | | | | | | | | (aa) |
|---|---|---|---|---|---|---|---|---|---|---|
| 4 | Asp | Lys | Thr | Glu | Ile | Pro | Thr | | | 7 |
| 13 | Ile | Gly | Ser | Glu | Ser | Thr | Glu | Asp | Gln | 9 |
| 17 | Ile | Pro | Asn | Pro | Ile | Gly | | | | 6 |
| 21 | Ile | Val | Pro | Asn | | | | | | 4 |
| 24 | Leu | Glu | Asp | Ser | Pro | Glu | | | | 6 |
| 30 | Asn | Gln | Glu | Gln | Pro | Ile | | | | 6 |
| 31 | Asn | Val | Pro | Gly | Glu | | | | | 5 |
| 32 | Pro | Phe | Pro | Gly | Pro | Ile | | | | 6 |
| 51 | Thr | Glu | Asp | Glu | Leu | | | | | 5 |
| 57 | Val | Pro | Ser | Glu | | | | | | 4 |
| 60 | Tyr | Pro | Phe | Pro | Gly | Pro | | | | 6 |
| 63 | Tyr | Pro | Ser | Gly | Ala | | | | | 5 |

In some embodiments, the peptide component may be present in the nutritional composition in an amount from about 0.2 g/100 Kcal to about 5.6 g/100 Kcal. In other embodiments the peptide component may be present in the nutritional composition in an amount from about 1 g/100 Kcal to about 4 g/100 Kcal. In still other embodiments, the peptide component may be present in the nutritional composition in an amount from about 2 g/100 Kcal to about 3 g/100 Kcal.

The peptide component disclosed herein may be formulated with other ingredients in the nutritional composition to provide appropriate nutrient levels for the target subject. In some embodiments, the peptide component is included in a nutritionally complete formula that is suitable to support normal growth.

The peptide component may be provided as an element of a protein equivalent source. In some embodiments, the peptides identified in Tables 1 and 2, may be provided by a protein equivalent source obtained from cow's milk proteins, including but not limited to bovine casein and bovine whey. In some embodiments, the protein equivalent source comprises hydrolyzed bovine casein or hydrolyzed bovine whey. Accordingly, in some embodiments, the peptides identified in Table 1 and Table 2 may be provided by a casein hydrolysate. Such peptides may be obtained by hydrolysis or may be synthesized in vitro by methods know to the skilled person.

A non-limiting example of a method of hydrolysis is disclosed herein. In some embodiments, this method may be used to obtain the protein hydrolysate and peptides of the present disclosure. The proteins are hydrolyzed using a proteolytic enzyme, Protease N. Protease N "Amano" is commercially available from Amano Enzyme U.S.A. Co., Ltd., Elgin, Ill. Protease N is a proteolytic enzyme preparation that is derived from the bacterial species *Bacillus subtilis*. The protease powder is specified as "not less than 150,000 units/g", meaning that one unit of Protease N is the amount of enzyme which produces an amino acid equivalent to 100 micrograms of tyrosine for 60 minutes at a pH of 7.0. To produce the infant formula of the present disclosure, Protease N can be used at levels of about 0.5% to about 1.0% by weight of the total protein being hydrolyzed.

The protein hydrolysis by Protease N is typically conducted at a temperature of about 50° C. to about 60° C. The hydrolysis occurs for a period of time so as to obtain a degree of hydrolysis between about 4% and 10%. In a particular embodiment, hydrolysis occurs for a period of time so as to obtain a degree of hydrolysis between about 6% and 9%. In another embodiment, hydrolysis occurs for a period of time so as to obtain a degree of hydrolysis of about 7.5%. This level of hydrolysis may take between about one half hour to about 3 hours.

A constant pH should be maintained during hydrolysis. In the method of the present disclosure, the pH is adjusted to and maintained between about 6.5 and 8. In a particular embodiment, the pH is maintained at about 7.0.

In order to maintain the optimal pH of the solution of whey protein, casein, water and Protease N, a caustic solution of sodium hydroxide and/or potassium hydroxide can be used to adjust the pH during hydrolysis. If sodium hydroxide is used to adjust the pH, the amount of sodium hydroxide added to the solution should be controlled to the level that it comprises less than about 0.3% of the total solid in the finished protein hydrolysate. A 10% potassium hydroxide solution can also be used to adjust the pH of the solution to the desired value, either before the enzyme is added or during the hydrolysis process in order to maintain the optimal pH.

The amount of caustic solution added to the solution during the protein hydrolysis can be controlled by a pH-stat or by adding the caustic solution continuously and proportionally. The hydrolysate can be manufactured by standard batch processes or by continuous processes.

To better ensure the consistent quality of the protein partial hydrolysate, the hydrolysate is subjected to enzyme deactivation to end the hydrolysis process. The enzyme deactivation step may consist include at heat treatment at a temperature of about 82° C. for about 10 minutes. Alternatively, the enzyme can be deactivated by heating the solution to a temperature of about 92° C. for about 5 seconds. After enzyme deactivation is complete, the hydrolysate can be stored in a liquid state at a temperature lower than 10° C.

In some embodiments, the protein equivalent source comprises a hydrolyzed protein, which includes partially hydrolyzed protein and extensively hydrolyzed protein, such as casein. In some embodiments, the protein equivalent source comprises a hydrolyzed protein including peptides having a molar mass distribution of greater than 500 Daltons. In some embodiments, the hydrolyzed protein comprises peptides having a molar mass distribution in the range of from about 500 Daltons to about 1,500 Daltons. Still, in some embodiments the hydrolyzed protein may comprise peptides having a molar mass distribution range of from about 500 Daltons to about 2,000 Daltons.

In some embodiments, the protein equivalent source may comprise the peptide component, intact protein, hydrolyzed protein, including partially hydrolyzed protein and/or extensively hydrolyzed protein, and combinations thereof. In some embodiments, 20% to 80% of the protein equivalent source comprises the peptide component disclosed herein. In some embodiments, 30% to 60% of the protein equivalent source comprises the peptide component disclosed herein. In still other embodiments, 40% to 50% of the protein equivalent source comprises the peptide component.

In some embodiments, 20% to 80% of the protein equivalent source comprises intact protein, partially hydrolyzed protein, extensively hydrolyzed protein, or combinations thereof. In some embodiments, 40% to 70% of the protein equivalent source comprises intact proteins, partially hydrolyzed proteins, extensively hydrolyzed protein, or a combination thereof. In still further embodiments, 50% to 60% of the protein equivalent source may comprise intact proteins, partially hydrolyzed protein, extensively hydrolyzed protein, or a combination thereof.

In some embodiments the protein equivalent source comprises partially hydrolyzed protein having a degree of hydrolysis of less than 40%. In still other embodiments, the protein equivalent source may comprise partially hydrolyzed protein having a degree of hydrolysis of less than 25%, or less than 15%.

In some embodiments, the nutritional composition comprises between about 1 g and about 7 g of a protein equivalent source per 100 Kcal. In other embodiments, the nutritional composition comprises between about 3.5 g and about 4.5 g of protein equivalent source per 100 Kcal.

Without being bound by any particular theory, the administration of a nutritional composition as disclosed herein may reduce allergic response and may improve tolerance to cow's milk allergy in certain subjects. In some embodiments, the combination of probiotic, such as LGG, dietary butyrate, and the protein equivalent source provide synergistic health benefits.

The nutritional composition(s) of the present disclosure may also comprise a carbohydrate source. Carbohydrate sources can be any used in the art, e.g., lactose, glucose, fructose, corn syrup solids, maltodextrins, sucrose, starch, rice syrup solids, and the like. The amount of carbohydrate in the nutritional composition typically can vary from between about 5 g and about 25 g/100 Kcal. In some embodiments, the amount of carbohydrate is between about 6 g and about 22 g/100 Kcal. In other embodiments, the amount of carbohydrate is between about 12 g and about 14 g/100 Kcal. In some embodiments, corn syrup solids are preferred. Moreover, hydrolyzed, partially hydrolyzed, and/or extensively hydrolyzed carbohydrates may be desirable for inclusion in the nutritional composition due to their easy digestibility. Specifically, hydrolyzed carbohydrates are less likely to contain allergenic epitopes.

Non-limiting examples of carbohydrate materials suitable for use herein include hydrolyzed or intact, naturally or chemically modified, starches sourced from corn, tapioca, rice or potato, in waxy or non-waxy forms. Non-limiting examples of suitable carbohydrates include various hydrolyzed starches characterized as hydrolyzed cornstarch, maltodextrin, maltose, corn syrup, dextrose, corn syrup solids, glucose, and various other glucose polymers and combinations thereof. Non-limiting examples of other suitable carbohydrates include those often referred to as sucrose, lactose, fructose, high fructose corn syrup, indigestible oligosaccharides such as fructooligosaccharides and combinations thereof.

The nutritional composition(s) of the disclosure may also comprise a protein source. The protein source can be any used in the art, e.g., nonfat milk, whey protein, casein, soy protein, hydrolyzed protein, amino acids, and the like. Bovine milk protein sources useful in practicing the present disclosure include, but are not limited to, milk protein powders, milk protein concentrates, milk protein isolates, nonfat milk solids, nonfat milk, nonfat dry milk, whey protein, whey protein isolates, whey protein concentrates, sweet whey, acid whey, casein, acid casein, caseinate (e.g. sodium caseinate, sodium calcium caseinate, calcium caseinate) and any combinations thereof.

In one embodiment, the proteins of the nutritional composition are provided as intact proteins. In other embodiments, the proteins are provided as a combination of both intact proteins and partially hydrolyzed proteins, with a degree of hydrolysis of between about 4% and 10%. In certain other embodiments, the proteins are more completely hydrolyzed. In still other embodiments, the protein source comprises amino acids. In yet another embodiment, the protein source may be supplemented with glutamine-containing peptides.

In a particular embodiment of the nutritional composition, the whey:casein ratio of the protein source is similar to that found in human breast milk. In an embodiment, the protein source comprises from about 40% to about 80% whey protein and from about 20% to about 60% casein.

In some embodiments, the nutritional composition comprises between about 1 g and about 7 g of a protein source per 100 Kcal. In other embodiments, the nutritional composition comprises between about 3.5 g and about 4.5 g of protein per 100 Kcal.

In some embodiments, the nutritional composition described herein comprises a fat source. The enriched lipid fraction described herein may be the sole fat source or may be used in combination with any other suitable fat or lipid source for the nutritional composition as known in the art. In certain embodiments, appropriate fat sources include, but are not limited to, animal sources, e.g., milk fat, butter, butter fat, egg yolk lipid; marine sources, such as fish oils, marine oils, single cell oils; vegetable and plant oils, such as corn oil, canola oil, sunflower oil, soybean oil, palm olein oil, coconut oil, high oleic sunflower oil, evening primrose oil, rapeseed oil, olive oil, flaxseed (linseed) oil, cottonseed oil, high oleic safflower oil, palm stearin, palm kernel oil, wheat germ oil; medium chain triglyceride oils and emulsions and esters of fatty acids; and any combinations thereof.

In some embodiment the nutritional composition comprises between about 1 g/100 Kcal to about 10 g/100 Kcal of a fat or lipid source. In some embodiments, the nutritional composition comprises between about 2 g/100 Kcal to about 7 g/100 Kcal of a fat source. In other embodiments the fat source may be present in an amount from about 2.5 g/100 Kcal to about 6 g/100 Kcal. In still other embodiments, the fat source may be present in the nutritional composition in an amount from about 3 g/100 Kcal to about 4 g/100 Kcal.

In some embodiments, the fat or lipid source comprises from about 10% to about 35% palm oil per the total amount of fat or lipid. In some embodiments, the fat or lipid source comprises from about 15% to about 30% palm oil per the total amount of fat or lipid. Yet in other embodiments, the fat or lipid source may comprise from about 18% to about 25% palm oil per the total amount of fat or lipid.

In certain embodiments, the fat or lipid source may be formulated to include from about 2% to about 16% soybean oil based on the total amount of fat or lipid. In some embodiments, the fat or lipid source may be formulated to include from about 4% to about 12% soybean oil based on the total amount of fat or lipid. In some embodiments, the fat or lipid source may be formulated to include from about 6% to about 10% soybean oil based on the total amount of fat or lipid.

In certain embodiments, the fat or lipid source may be formulated to include from about 2% to about 16% coconut oil based on the total amount of fat or lipid. In some embodiments, the fat or lipid source may be formulated to include from about 4% to about 12% coconut oil based on the total amount of fat or lipid. In some embodiments, the fat or lipid source may be formulated to include from about 6% to about 10% coconut oil based on the total amount of fat or lipid.

In certain embodiments, the fat or lipid source may be formulated to include from about 2% to about 16% sunflower oil based on the total amount of fat or lipid. In some embodiments, the fat or lipid source may be formulated to include from about 4% to about 12% sunflower oil based on the total amount of fat or lipid. In some embodiments, the fat or lipid source may be formulated to include from about 6% to about 10% sunflower oil based on the total amount of fat or lipid.

In some embodiments, the oils, i.e. sunflower oil, soybean oil, sunflower oil, palm oil, etc. are meant to cover fortified versions of such oils known in the art. For example, in certain embodiments, the use of sunflower oil may include high oleic sunflower oil. In other examples, the use of such oils may be fortified with certain fatty acids, as known in the art, and may be used in the fat or lipid source disclosed herein.

In some embodiments the nutritional composition may also include a source of LCPUFAs. In one embodiment the amount of LCPUFA in the nutritional composition is advantageously at least about 5 mg/100 Kcal, and may vary from about 5 mg/100 Kcal to about 100 mg/100 Kcal, more preferably from about 10 mg/100 Kcal to about 50 mg/100 Kcal. Non-limiting examples of LCPUFAs include, but are not limited to, DHA, ARA, linoleic (18:2 n-6), γ-linolenic (18:3 n-6), dihomo-γ-linolenic (20:3 n-6) acids in the n-6 pathway, α-linolenic (18:3 n-3), stearidonic (18:4 n-3), eicosatetraenoic (20:4 n-3), eicosapentaenoic (20:5 n-3), and docosapentaenoic (22:6 n-3).

In some embodiments, the LCPUFA included in the nutritional composition may comprise DHA. In one embodiment the amount of DHA in the nutritional composition is advantageously at least about 17 mg/100 Kcal, and may vary from about 5 mg/100 Kcal to about 75 mg/100 Kcal, more preferably from about 10 mg/100 Kcal to about 50 mg/100 Kcal.

In another embodiment, especially if the nutritional composition is an infant formula, the nutritional composition is supplemented with both DHA and ARA. In this embodiment, the weight ratio of ARA:DHA may be between about 1:3 and about 9:1. In a particular embodiment, the ratio of ARA:DHA is from about 1:2 to about 4:1.

The DHA and ARA can be in natural form, provided that the remainder of the LCPUFA source does not result in any substantial deleterious effect on the infant. Alternatively, the DHA and ARA can be used in refined form.

The disclosed nutritional composition described herein can, in some embodiments, also comprise a source of β-glucan. Glucans are polysaccharides, specifically polymers of glucose, which are naturally occurring and may be found in cell walls of bacteria, yeast, fungi, and plants. Beta glucans (β-glucans) are themselves a diverse subset of glucose polymers, which are made up of chains of glucose monomers linked together via beta-type glycosidic bonds to form complex carbohydrates.

β-1,3-glucans are carbohydrate polymers purified from, for example, yeast, mushroom, bacteria, algae, or cereals. (Stone B A, Clarke A E. Chemistry and Biology of (1-3)-Beta-Glucans. London:Portland Press Ltd; 1993.) The chemical structure of β-1,3-glucan depends on the source of the β-1,3-glucan. Moreover, various physiochemical parameters, such as solubility, primary structure, molecular weight, and branching, play a role in biological activities of β-1,3-glucans. (Yadomae T., Structure and biological activities of fungal beta-1,3-glucans. Yakugaku Zasshi. 2000; 120:413-431.)

β-1,3-glucans are naturally occurring polysaccharides, with or without β-1,6-glucose side chains that are found in the cell walls of a variety of plants, yeasts, fungi and bacteria. β-1,3;1,6-glucans are those containing glucose units with (1,3) links having side chains attached at the (1,6) position(s). β-1,3;1,6 glucans are a heterogeneous group of glucose polymers that share structural commonalties, including a backbone of straight chain glucose units linked by a β-1,3 bond with β-1,6-linked glucose branches extending from this backbone. While this is the basic structure for the presently described class of β-glucans, some variations may exist. For example, certain yeast β-glucans have additional regions of β(1,3) branching extending from the β(1,6) branches, which add further complexity to their respective structures.

β-glucans derived from baker's yeast, *Saccharomyces cerevisiae*, are made up of chains of D-glucose molecules connected at the 1 and 3 positions, having side chains of glucose attached at the 1 and 6 positions. Yeast-derived β-glucan is an insoluble, fiber-like, complex sugar having the general structure of a linear chain of glucose units with a β-1,3 backbone interspersed with β-1,6 side chains that are generally 6-8 glucose units in length. More specifically, β-glucan derived from baker's yeast is poly-(1,6)-β-D-glucopyranosyl-(1,3)-β-D-glucopyranose.

Furthermore, β-glucans are well tolerated and do not produce or cause excess gas, abdominal distension, bloating or diarrhea in pediatric subjects. Addition of β-glucan to a nutritional composition for a pediatric subject, such as an infant formula, a growing-up milk or another children's nutritional product, will improve the subject's immune response by increasing resistance against invading pathogens and therefore maintaining or improving overall health.

In some embodiments, the β-glucan is β-1,3;1,6-glucan. In some embodiments, the β-1,3;1,6-glucan is derived from baker's yeast. The nutritional composition may comprise whole glucan particle β-glucan, particulate β-glucan, PGG-glucan (poly-1,6-β-D-glucopyranosyl-1,3-β-D-glucopyranose) or any mixture thereof.

In some embodiments, the amount of β-glucan in the nutritional composition is between about 3 mg and about 17 mg per 100 Kcal. In another embodiment the amount of β-glucan is between about 6 mg and about 17 mg per 100 Kcal.

The disclosed nutritional composition described herein, can, in some embodiments also comprise an effective amount of iron. The iron may comprise encapsulated iron forms, such as encapsulated ferrous fumarate or encapsulated ferrous sulfate or less reactive iron forms, such as ferric pyrophosphate or ferric orthophosphate.

One or more vitamins and/or minerals may also be added in to the nutritional composition in amounts sufficient to supply the daily nutritional requirements of a subject. It is to be understood by one of ordinary skill in the art that vitamin and mineral requirements will vary, for example, based on the age of the child. For instance, an infant may have different vitamin and mineral requirements than a child between the ages of one and thirteen years. Thus, the embodiments are not intended to limit the nutritional composition to a particular age group but, rather, to provide a range of acceptable vitamin and mineral components.

In embodiments providing a nutritional composition for a child, the composition may optionally include, but is not limited to, one or more of the following vitamins or derivations thereof: vitamin $B_1$ (thiamin, thiamin pyrophosphate, TPP, thiamin triphosphate, TTP, thiamin hydrochloride, thiamin mononitrate), vitamin $B_2$ (riboflavin, flavin mononucleotide, FMN, flavin adenine dinucleotide, FAD, lactoflavin, ovoflavin), vitamin $B_3$ (niacin, nicotinic acid, nicotinamide, niacinamide, nicotinamide adenine dinucleotide, NAD, nicotinic acid mononucleotide, NicMN, pyridine-3-carboxylic acid), vitamin $B_3$-precursor tryptophan, vitamin $B_6$ (pyridoxine, pyridoxal, pyridoxamine, pyridoxine hydrochloride), pantothenic acid (pantothenate, panthenol), folate (folic acid, folacin, pteroylglutamic acid), vitamin $B_{12}$ (cobalamin, methylcobalamin, deoxyadenosylcobalamin, cyanocobalamin, hydroxycobalamin, adenosylcobalamin), biotin, vitamin C (ascorbic acid), vitamin A (retinol, retinyl acetate, retinyl palmitate, retinyl esters with other long-chain fatty acids, retinal, retinoic acid, retinol esters), vitamin D (calciferol, cholecalciferol, vitamin $D_3$, 1,25,-dihydroxyvitamin D), vitamin E (α-tocopherol, α-tocopherol acetate, α-tocopherol succinate, α-tocopherol nicotinate, α-tocopherol), vitamin K (vitamin $K_1$, phylloquinone, naphthoquinone, vitamin $K_2$, menaquinone-7, vitamin $K_3$, menaquinone-4, menadione, menaquinone-8, menaquinone-8H, menaquinone-9, menaquinone-9H, menaquinone-10, menaquinone-11, menaquinone-12, menaquinone-13), choline, inositol, β-carotene and any combinations thereof.

In embodiments providing a children's nutritional product, such as a growing-up milk, the composition may optionally include, but is not limited to, one or more of the following minerals or derivations thereof: boron, calcium, calcium acetate, calcium gluconate, calcium chloride, calcium lactate, calcium phosphate, calcium sulfate, chloride, chromium, chromium chloride, chromium picolonate, copper, copper sulfate, copper gluconate, cupric sulfate, fluoride, iron, carbonyl iron, ferric iron, ferrous fumarate, ferric orthophosphate, iron trituration, polysaccharide iron, iodide, iodine, magnesium, magnesium carbonate, magnesium hydroxide, magnesium oxide, magnesium stearate, magnesium sulfate, manganese, molybdenum, phosphorus, potassium, potassium phosphate, potassium iodide, potassium chloride, potassium acetate, selenium, sulfur, sodium, docusate sodium, sodium chloride, sodium selenate, sodium molybdate, zinc, zinc oxide, zinc sulfate and mixtures thereof. Non-limiting exemplary derivatives of mineral compounds include salts, alkaline salts, esters and chelates of any mineral compound.

The minerals can be added to growing-up milks or to other children's nutritional compositions in the form of salts such as calcium phosphate, calcium glycerol phosphate, sodium citrate, potassium chloride, potassium phosphate, magnesium phosphate, ferrous sulfate, zinc sulfate, cupric sulfate, manganese sulfate, and sodium selenite. Additional vitamins and minerals can be added as known within the art.

The nutritional compositions of the present disclosure may optionally include one or more of the following flavoring agents, including, but not limited to, flavored extracts, volatile oils, cocoa or chocolate flavorings, peanut butter flavoring, cookie crumbs, vanilla or any commercially available flavoring. Examples of useful flavorings include, but are not limited to, pure anise extract, imitation banana extract, imitation cherry extract, chocolate extract, pure lemon extract, pure orange extract, pure peppermint extract, honey, imitation pineapple extract, imitation rum extract, imitation strawberry extract, or vanilla extract; or volatile oils, such as balm oil, bay oil, bergamot oil, cedarwood oil, cherry oil, cinnamon oil, clove oil, or peppermint oil; peanut butter, chocolate flavoring, vanilla cookie crumb, butterscotch, toffee, and mixtures thereof. The amounts of flavoring agent can vary greatly depending upon the flavoring agent used. The type and amount of flavoring agent can be selected as is known in the art.

The nutritional compositions of the present disclosure may optionally include one or more emulsifiers that may be added for stability of the final product. Examples of suitable emulsifiers include, but are not limited to, lecithin (e.g., from egg or soy), alpha lactalbumin and/or mono- and di-glycerides, and mixtures thereof. Other emulsifiers are readily apparent to the skilled artisan and selection of suitable emulsifier(s) will depend, in part, upon the formulation and final product.

The nutritional compositions of the present disclosure may optionally include one or more preservatives that may also be added to extend product shelf life. Suitable preservatives include, but are not limited to, potassium sorbate, sodium sorbate, potassium benzoate, sodium benzoate, calcium disodium EDTA, and mixtures thereof.

The nutritional compositions of the present disclosure may optionally include one or more stabilizers. Suitable stabilizers for use in practicing the nutritional composition of the present disclosure include, but are not limited to, gum arabic, gum ghatti, gum karaya, gum tragacanth, agar, furcellaran, guar gum, gellan gum, locust bean gum, pectin, low methoxyl pectin, gelatin, microcrystalline cellulose, CMC (sodium carboxymethylcellulose), methylcellulose hydroxypropyl methyl cellulose, hydroxypropyl cellulose, DATEM (diacetyl tartaric acid esters of mono- and diglycerides), dextran, carrageenans, and mixtures thereof.

The nutritional compositions of the disclosure may provide minimal, partial or total nutritional support. The compositions may be nutritional supplements or meal replacements. The compositions may, but need not, be nutritionally complete. In an embodiment, the nutritional composition of the disclosure is nutritionally complete and contains suitable types and amounts of lipid, carbohydrate, protein, vitamins and minerals. The amount of lipid or fat typically can vary from about 1 to about 25 g/100 Kcal. The amount of protein typically can vary from about 1 to about 7 g/100 Kcal. The amount of carbohydrate typically can vary from about 6 to about 22 g/100 Kcal.

In an embodiment, the children's nutritional composition may contain between about 10 and about 50% of the maximum dietary recommendation for any given country, or between about 10 and about 50% of the average dietary recommendation for a group of countries, per serving of vitamins A, C, and E, zinc, iron, iodine, selenium, and choline. In another embodiment, the children's nutritional composition may supply about 10-30% of the maximum dietary recommendation for any given country, or about 10-30% of the average dietary recommendation for a group of countries, per serving of B-vitamins. In yet another embodiment, the levels of vitamin D, calcium, magnesium, phosphorus, and potassium in the children's nutritional product may correspond with the average levels found in milk. In other embodiments, other nutrients in the children's nutritional composition may be present at about 20% of the maximum dietary recommendation for any given country, or about 20% of the average dietary recommendation for a group of countries, per serving.

In some embodiments the nutritional composition is an infant formula. Infant formulas are fortified nutritional compositions for an infant. The content of an infant formula is dictated by federal regulations, which define macronutrient, vitamin, mineral, and other ingredient levels in an effort to simulate the nutritional and other properties of human breast milk. Infant formulas are designed to support overall health and development in a pediatric human subject, such as an infant or a child.

In some embodiments, the nutritional composition of the present disclosure is a growing-up milk. Growing-up milks are fortified milk-based beverages intended for children over 1 year of age (typically from 1-3 years of age, from 4-6 years of age or from 1-6 years of age). They are not medical foods and are not intended as a meal replacement or a supplement to address a particular nutritional deficiency. Instead, growing-up milks are designed with the intent to serve as a complement to a diverse diet to provide additional insurance that a child achieves continual, daily intake of all essential vitamins and minerals, macronutrients plus additional functional dietary components, such as non-essential nutrients that have purported health-promoting properties.

The exact composition of a growing-up milk or other nutritional composition according to the present disclosure can vary from market-to-market, depending on local regulations and dietary intake information of the population of interest. In some embodiments, nutritional compositions according to the disclosure consist of a milk protein source, such as whole or skim milk, plus added sugar and sweeteners to achieve desired sensory properties, and added vitamins and minerals. The fat composition includes an enriched lipid fraction derived from milk. Total protein can be targeted to match that of human milk, cow milk or a lower value. Total carbohydrate is usually targeted to provide as little added sugar, such as sucrose or fructose, as possible to achieve an acceptable taste. Typically, Vitamin A, calcium and Vitamin D are added at levels to match the nutrient contribution of regional cow milk. Otherwise, in some embodiments, vitamins and minerals can be added at levels that provide approximately 20% of the dietary reference intake (DRI) or 20% of the Daily Value (DV) per serving. Moreover, nutrient values can vary between markets depending on the identified nutritional needs of the intended population, raw material contributions and regional regulations.

The disclosed nutritional composition(s) may be provided in any form known in the art, such as a powder, a gel, a suspension, a paste, a solid, a liquid, a liquid concentrate, a reconstituteable powdered milk substitute or a ready-to-use product. The nutritional composition may, in certain embodiments, comprise a nutritional supplement, children's nutritional product, infant formula, human milk fortifier, growing-up milk or any other nutritional composition designed for an infant or a pediatric subject. Nutritional compositions of the present disclosure include, for example, orally-ingestible, health-promoting substances including, for example, foods, beverages, tablets, capsules and powders. Moreover, the nutritional composition of the present disclosure may be standardized to a specific caloric content, it may be provided as a ready-to-use product, or it may be provided in a concentrated form. In some embodiments, the nutritional composition is in powder form with a particle size in the range of 5 µm to 1500 µm, more preferably in the range of 10 µm to 300 µm.

The nutritional compositions of the present disclosure may be provided in a suitable container system. For example, non-limiting examples of suitable container systems include plastic containers, metal containers, foil pouches, plastic pouches, multi-layered pouches, and combinations thereof. In certain embodiments, the nutritional composition may be a powdered composition that is contained within a plastic container. In certain other embodiments, the nutritional composition may be contained within a plastic pouch located inside a plastic container.

The nutritional compositions described herein, in some embodiments, advantageously reduce the incidence of allergic reaction and improve tolerance to cow's milk allergy in a subject. Further, in some embodiments, the nutritional compositions advantageously reduce the inflammatory response caused by allergy in a subject. Accordingly, the disclosure relates to methods of improving tolerance to cow's milk allergy in a subject. Further, the disclosure relates to methods for the dietary management of allergic diseases and/or allergic reaction in a subject via administration of the nutritional compositions including a probiotic, such as LGG, and dietary butyrate as disclosed herein.

In some embodiments, the method comprises the step of subjecting the target subject to cow's milk and then providing the nutritional composition disclosed herein including a probiotic and dietary butyrate to the target subject. In certain embodiments, after the target subject has been subjected to cow's milk, the target subject may be provided with a nutritional composition that includes a probiotic and dietary butyrate and a protein equivalent source as disclosed herein. In certain embodiments, the target subject, after being exposed to cow's milk or other allergen, may be administered a nutritional composition comprising probiotic and dietary butyrate, and a protein equivalent source. In certain embodiments, the protein equivalent source may be substantially free of whole and/or intact protein. In certain other embodiments, the protein equivalent source may comprise hydrolyzed protein, amino acids, the peptide component disclosed herein, and combinations thereof. In some embodiments, the nutritional composition includes a protein equivalent source includes amino acids and no hydrolyzed or whole/intact protein.

In some embodiments, the target subject is not subjected to cow's milk or an allergen prior to administration of the nutritional composition. Thus, in some embodiments, the method is directed to reducing allergic response in a target subject via providing the nutritional compositions disclosed herein including dietary butyrate to the target subject, and subsequently exposing the target subject to cow's milk or other allergen.

The nutritional compositions described herein, in some embodiments, advantageously reduce the inflammatory response in a subject. Accordingly, the disclosure relates to methods of reducing a proinflammatory response in a subject by administering to a subject a nutritional composition containing the protein equivalent source described herein in combination with probiotic and dietary butyrate. For example, the present methods may reduce the production of proinflammatory cytokines in a subject.

In some embodiments, the method for reducing an inflammatory response in a subject comprises administering to a subject a nutritional composition comprising a carbohydrate source, a protein equivalent source, fat source, probiotic, and dietary butyrate, wherein the protein equivalent source includes a peptide component comprising SEQ ID NO 4, SEQ ID NO 13, SEQ ID NO 17, SEQ ID NO 21, SEQ ID NO 24, SEQ ID NO 30, SEQ ID NO 31, SEQ ID NO 32, SEQ ID NO 51, SEQ ID NO 57, SEQ ID NO 60, and SEQ ID NO 63. In some embodiments, the peptide component may comprise additional peptides disclosed in Table 1. For example, the composition may include at least 10 additional peptides disclosed in Table 1. In some embodiments, 20% to 80% of the protein equivalent source comprises the peptide component, and 20% to 80% of the protein equivalent source comprises an intact protein, a partially hydrolyzed protein, and combinations thereof.

In another embodiment, the method comprises administering to a subject a nutritional composition, wherein 20% to 80% of the protein equivalent source includes a peptide component comprising at least 3 peptides selected from the group consisting of SEQ ID NO 4, SEQ ID NO 13, SEQ ID NO 17, SEQ ID NO 21, SEQ ID NO 24, SEQ ID NO 30, SEQ ID NO 31, SEQ ID NO 32, SEQ ID NO 51, SEQ ID NO 57, SEQ ID NO 60, and SEQ ID NO 63, and at least 5 additional peptides selected from Table 1; and wherein 20% to 80% of the protein equivalent source comprises an intact protein, a partially hydrolyzed protein, or combinations thereof.

In yet other embodiments, the method for reducing the inflammatory response includes providing a nutritional composition comprising a peptide component from Table 1, wherein the peptide component is derived from a casein hydrolysate having a molar mass distribution of greater than 500 Daltons. In some embodiments, the molar mass distribution of the casein hydrolysate is in a range of 500 to 2000 Daltons. In other embodiments, the method for reducing the inflammatory response includes providing a nutritional composition comprising the peptide component described herein, wherein the peptide component is derived from a casein hydrolysate that does not include peptides having a molar mass distribution of less than 200 Daltons.

In some embodiments the target subject may be a pediatric subject. Further, in one embodiment, the nutritional composition provided to the pediatric subject may be an infant formula. The peptide component identified herein, probiotic and dietary butyrate as disclosed herein may be added to the infant formula and, further, each may be selected from a specific source and concentrations thereof may be adjusted to maximize health benefits. In another embodiment of this method, the nutritional composition comprising the peptide component disclosed herein, probiotic and dietary butyrate is a growing up milk.

In embodiments when the nutritional composition is an infant formula, the composition may advantageously reduce a pro-inflammatory response in the infant, and thereby reduce the incidence of inflammatory disease. Moreover, the reduction in inflammatory disease may last throughout childhood and into adulthood. Similarly, when the nutritional composition is a growing-up milk, a child who ingests the growing-up milk may experience a reduction in the incidence of inflammatory disease in adulthood, as well as during childhood.

In certain embodiments, the disclosure is directed to a method for improving the absorption of butyrate in a target subject by providing or administering the nutritional compositions disclosed herein including probiotic and dietary butyrate to the target subject. In some embodiments, the target subject is a pediatric subject or an infant. In some embodiments, the nutritional composition is an infant formula or a growing-up milk.

All combinations of method or process steps as used herein can be performed in any order, unless otherwise specified or clearly implied to the contrary by the context in which the referenced combination is made.

The methods and compositions of the present disclosure, including components thereof, can comprise, consist of, or consist essentially of the essential elements and limitations of the embodiments described herein, as well as any additional or optional ingredients, components or limitations described herein or otherwise useful in nutritional compositions.

Formulation examples are provided to illustrate some embodiments of the nutritional composition of the present disclosure but should not be interpreted as any limitation thereon. Other embodiments within the scope of the claims herein will be apparent to one skilled in the art from the consideration of the specification or practice of the nutritional composition or methods disclosed herein. It is intended that the specification, together with the example, be considered to be exemplary only, with the scope and spirit of the disclosure being indicated by the claims which follow the example.

FORMULATION EXAMPLES

Table 3 provides an example embodiment of a peptide component including 8 peptides from Table 1.

TABLE 3

| Example peptide component |
| Example of Selected Peptides for Peptide Component |
| --- |
| SEQ ID NO 5 |
| SEQ ID NO 24 |
| SEQ ID NO 33 |
| SEQ ID NO 56 |
| SEQ ID NO 64 |
| SEQ ID NO 13 |
| SEQ ID NO 24 |
| SEQ ID NO 60 |

Table 4 provides an example embodiment of a peptide component including certain peptides from Table 1.

TABLE 4

| Example peptide component |
| Example of Selected Peptides for Peptide Component |
| --- |
| SEQ ID NO 13 |
| SEQ ID NO 24 |
| SEQ ID NO 60 |
| SEQ ID NO 5 |
| SEQ ID NO 11 |
| SEQ ID NO 22 |
| SEQ ID NO 25 |
| SEQ ID NO 33 |
| SEQ ID NO 45 |
| SEQ ID NO 46 |
| SEQ ID NO 47 |
| SEQ ID NO 48 |
| SEQ ID NO 52 |
| SEQ ID NO 34 |
| SEQ ID NO 36 |
| SEQ ID NO 61 |
| SEQ ID NO 62 |
| SEQ ID NO 64 |

TABLE 5

Nutrition profile of an example nutritional composition including dietary butyrate

| | per 100 Kcal | |
| --- | --- | --- |
| Nutrient | Minimum | Maximum |
| Protein Equivalent Source (g) | 1.0 | 7.0 |
| Dietary butyrate (mg) | 22 | 280 |
| *Lactobacillus rhamnosus* GG (cfu) | $1 \times 10^4$ | $1.5 \times 10^{12}$ |
| Carbohydrates (g) | 6 | 22 |
| Fat (g) | 1.3 | 7.2 |
| Prebiotic (g) | 0.3 | 1.2 |
| DHA (g) | 4 | 22 |
| Beta glucan (mg) | 2.9 | 17 |
| Probiotics (cfu) | 0.5 | 5.0 |
| Vitamin A (IU) | $9.60 \times 10^5$ | $3.80 \times 10^8$ |
| Vitamin D (IU) | 134 | 921 |
| Vitamin E (IU) | 22 | 126 |
| Vitamin K (mcg) | 0.8 | 5.4 |
| Thiamin (mcg) | 2.9 | 18 |
| Riboflavin (mcg) | 63 | 328 |
| Vitamin B6 (mcg) | 68 | 420 |
| Vitamin B12 (mcg) | 52 | 397 |
| Niacin (mcg) | 0.2 | 0.9 |
| Folic acid (mcg) | 690 | 5881 |
| Panthothenic acid (mcg) | 8 | 66 |
| Biotin (mcg) | 232 | 1211 |
| Vitamin C (mg) | 1.4 | 5.5 |
| Choline (mg) | 4.9 | 24 |
| Calcium (mg) | 4.9 | 43 |
| Phosphorus (mg) | 68 | 297 |
| Magnesium (mg) | 54 | 210 |
| Sodium (mg) | 4.9 | 34 |
| Potassium (mg) | 24 | 88 |
| Chloride (mg) | 82 | 346 |
| Iodine (mcg) | 53 | 237 |
| Iron (mg) | 8.9 | 79 |
| Zinc (mg) | 0.7 | 2.8 |
| Manganese (mcg) | 0.7 | 2.4 |
| Copper (mcg) | 7.2 | 41 |

Table 5, illustrated below, provides an example embodiment of the nutritional profile of a nutritional composition including PDX/GOS and dietary butyrate and describes the amount of each ingredient to be included per 100 Kcal serving of nutritional composition.

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

Although embodiments of the disclosure have been described using specific terms, devices, and methods, such description is for illustrative purposes only. The words used are words of description rather than of limitation. It is to be understood that changes and variations may be made by those of ordinary skill in the art without departing from the spirit or the scope of the present disclosure, which is set forth in the following claims. In addition, it should be understood that aspects of the various embodiments may be interchanged in whole or in part. Therefore, the spirit and scope of the appended claims should not be limited to the description of the versions contained therein.

What is claimed is:

1. A nutritional composition, comprising per 100 Kcal:
   (i) between about 6 g and about 22 g of a carbohydrate source;
   (ii) between about 1 g and about 7 g of a protein source;
   (iii) between about 1 g and about 10.3 g of a fat source;
   (iv) between about $1 \times 10^4$ CFU to about $1.5 \times 10^{12}$ CFU of *Lactobacillus rhamnosus* GG; and
   (v) between about 22 mg and 280 mg of dietary butyrate.

2. The nutritional composition of claim 1, further comprising one or more long chain polyunsaturated fatty acids.

3. The nutritional composition of claim 1, further comprising one or more prebiotics.

4. The nutritional composition of claim 1, wherein the nutritional composition further comprises a component for stimulating endogenous butyrate production, wherein the component for stimulating endogenous butyrate production comprises polydextrose and galacto-oligosaccharides.

5. The nutritional composition of claim 1, wherein the dietary butyrate comprises one or more of the following compounds selected from the group consisting of N-(1-carbamoyl-2-phenyl-ethyl) butyramide; N-(1-butyroyl-carbamoyl-2-phenyl-ethyl)butyramide; 5-benzyl-2-propyl-1H-imidazol-4(5H)-one; N-(1-oxo-3-phenyl-1-(piperidin-1-yl)propan-2-yl)butyramide; N-(1-oxo-3-phenyl-1-(pyrrolidin-1-yl)propan-2-yl)butyramide; N-(1-(methylcarbamoyl)-2-phenylethyl) butyramide; N-(1-(ethylcarbamoyl)-2-phenylethyl)butyramide; N-(1-(propylcarbamoyl)-2-phenylethyl)butyramide; N-(1-(butylcarbamoyl)-2-phenylethyl)butyramide; N-(1-(pentylcarbamoyl)-2-phenylethyl)butyramide; N-(1-carbamoyl-2-phenylethyl)-N-methyl butyramide; N-(1-carbamoyl-2-phenylethyl)-N-ethylbutyramide; N-(1-carbamoyl-2-phenylethyl)-N-propylbutyramide; and/or corresponding mixtures and corresponding salts of pharmaceutically acceptable bases or acids, pure diastereoisomeric forms and enantiomeric forms or mixtures thereof.

6. The nutritional composition of claim 2, wherein the one or more long chain polyunsaturated fatty acids comprises docosahexaenoic acid, arachidonic acid, or combinations thereof.

7. The nutritional composition of claim 1, further comprising a prebiotic comprising β-glucan.

* * * * *